United States Patent
Dailey, Jr. et al.

(10) Patent No.: US 7,830,513 B2
(45) Date of Patent: Nov. 9, 2010

(54) OPTICAL INTERROGATION SYSTEM AND MICROPLATE POSITION CORRECTION METHOD

(75) Inventors: Michael J. Dailey, Jr., Painted Post, NY (US); Garrett A. Piech, Horseheads, NY (US); Gordon M. Shedd, Lawrenceville, PA (US); Michael B. Webb, Lindley, NY (US); Elvis A. Zambrano, Corning, NY (US)

(73) Assignee: Corning Incorporated, Corning, NY (US)

( * ) Notice: Subject to any disclaimer, the term of this patent is extended or adjusted under 35 U.S.C. 154(b) by 551 days.

(21) Appl. No.: 11/900,315

(22) Filed: Sep. 11, 2007

(65) Prior Publication Data
US 2009/0027693 A1 Jan. 29, 2009

Related U.S. Application Data

(60) Provisional application No. 60/844,736, filed on Sep. 15, 2006.

(51) Int. Cl.
| | |
|---|---|
| G01B 11/00 | (2006.01) |
| G01B 11/14 | (2006.01) |
| G01J 3/30 | (2006.01) |
| G01J 3/28 | (2006.01) |
| G01N 21/00 | (2006.01) |
| G01N 21/75 | (2006.01) |
| G01N 21/62 | (2006.01) |
| G01N 21/76 | (2006.01) |

(52) U.S. Cl. ............... 356/399; 356/317; 356/326; 356/614; 422/82.05; 436/164; 436/171; 436/172

(58) Field of Classification Search .......... None
See application file for complete search history.

(56) References Cited

U.S. PATENT DOCUMENTS

| | | | |
|---|---|---|---|
| 6,310,687 B1* | 10/2001 | Stumbo et al. | 356/317 |
| 6,488,892 B1* | 12/2002 | Burton et al. | 422/82.05 |
| 6,633,659 B1* | 10/2003 | Zhou | 382/129 |
| 6,635,886 B1* | 10/2003 | Rushbrooke et al. | 250/458.1 |
| 2005/0239104 A1* | 10/2005 | Ferea et al. | 435/6 |
| 2006/0139641 A1 | 6/2006 | Gollier et al. | 356/399 |
| 2006/0141611 A1 | 6/2006 | Frutos et al. | 435/287.2 |
| 2006/0180750 A1 | 8/2006 | Gollier et al. | 250/227.11 |
| 2006/0263777 A1* | 11/2006 | Tong | 435/6 |
| 2007/0020152 A1 | 1/2007 | Costello, III et al. | 422/104 |
| 2007/0020689 A1 | 1/2007 | Caracci et al. | 435/7.1 |

OTHER PUBLICATIONS

Jacques Gollier et al., "Optically Readable Microplate", U. S. App. No. 60/755,808, filed Dec. 30, 2005.
Jacques Gollier et al., Optimized Method For LID Biosensor Resonance Detection, U.S. Appl. No. 60/781,397, filed Mar. 10, 2006.

(Continued)

*Primary Examiner*—Tarifur Chowdhury
*Assistant Examiner*—Gordon J Stock, Jr.
(74) *Attorney, Agent, or Firm*—Gregory B. Butler; Thomad R. Beall

(57) ABSTRACT

An optical interrogation system and method are described herein that are capable of detecting and correcting a positional misalignment of a label independent detection (LID) microplate so that the LID microplate can be properly interrogated after being removed from and then re-inserted back into a microplate holder/XY translation stage.

33 Claims, 19 Drawing Sheets

OTHER PUBLICATIONS

Mark F. Krol et al., "Screening System and Method For Analyzing a Plurality of Biosensors", U.S. Appl. No. 11/521,771, filed Sep. 15, 2006.

Jacques Gollier et al., "Swept Wavelength Imaging Optical Interrogation System and Method For Using Same", U.S. Serial No. 711,207, filed Feb. 27, 2007.

* cited by examiner

OPTICAL INTERROGATION SYSTEM AND MICROPLATE POSITION CORRECTION METHOD

CLAIM BENEFIT OF PRIOR FILED U.S. APPLICATION

This application claims the benefit of U.S. Provisional Application Ser. No. 60/844,736 filed on Sep. 15, 2006 and entitled "Active Microplate Position Correction for Biosensors". The contents of this document are incorporated by reference herein.

CROSS REFERENCE TO RELATED APPLICATIONS

This application is related to the following patent applications:

1. U.S. patent application Ser. No. 11/058,155 filed Feb. 14, 2005 and entitled "Single Mode (SM) Fiber Optical Reader System and Method for Interrogating Resonant Waveguide-Grating Sensor(s)", Publication No. US-2006-0180750 A1, Published Aug. 17, 2006.

2: U.S. patent application Ser. No. 11/027,547 filed Dec. 29, 2004 and entitled "Spatially Scanned Optical Reader System and Method for Using Same", Ser. No. 11/027,547, Filed Dec. 29, 2004, Publication No. US-2006-0141611 A1, Published Jun. 29, 2006.

3: U.S. patent application Ser. No. 11/210,920 filed Aug. 23, 2005 and entitled "Optical Reader System and Method for Monitoring and Correcting Lateral and Angular Misalignments of Label Independent Biosensors", Publication No. US-2006-0139641 A1, Published Jun. 29, 2006.

4: U.S. Patent Application Ser. No. 60/781,397 filed Mar. 10, 2006 and entitled "Optimized Method for LID Biosensor Resonance Detection".

The contents of these four references are hereby incorporated by reference herein.

TECHNICAL FIELD

The present invention relates to an optical interrogation system and method for detecting and correcting a positional misalignment of a label independent detection (LID) microplate so that the LID microplate can be properly interrogated after being removed from and then re-inserted back into a microplate holder/XY translation stage.

BACKGROUND

A major challenge today is to design an optical interrogation system that can properly interrogate a label independent detection (LID) microplate after it has been removed from and then re-inserted back into a microplate holder/XY translation stage. In particular, what is needed is an optical interrogation system that can take into account a positional misalignment of a re-positioned LID microplate so it can properly interrogate biosensors located within the wells of the re-positioned LID microplate. This need and other needs are addressed by the optical interrogation system and the method of the present invention.

SUMMARY

The present invention relates to an optical interrogation system and method capable of detecting and correcting a positional misalignment of a LID microplate so that the LID microplate can be properly interrogated after being removed from and then re-inserted back into a microplate holder/XY translation stage. In one embodiment, the method includes the following steps: (a) placing the microplate onto a holder; (b) scanning an optical beam across a row of the biosensors within the microplate to determine a first position of the microplate and to obtain a first set of interrogation wavelength/angular measurements (note: if desired this step can be performed in two separate scanning steps); (c) removing the microplate from the holder; (d) re-inserting the microplate back onto the holder; (e) re-scanning the optical beam across the row of the biosensors within the microplate to determine a second position of the microplate; (f) determining a position deviation of the microplate by comparing the first position and the second position of the microplate; (g) calculating a scan trajectory to take into account the position deviation of the microplate; (h) re-scanning the optical beam using the calculated scan trajectory over the row of the biosensors within the microplate to obtain a second set of interrogation wavelength/angular measurements; and (i) comparing the first set of interrogation wavelength/angular measurements and the second set of interrogation wavelength/angular measurements to determine whether or not a biological substance is present or a biomolecular event occurred on one or more of the biosensors within the microplate. An optical interrogation system that is capable of implementing this method is also described herein.

In another embodiment, the method includes the following steps: (a) placing the microplate onto a holder; (b) scanning an optical beam across a row of fiducial markings/reference sensors within the microplate to determine a first position of the microplate; (c) scanning the optical beam across a row of the biosensors within the microplate to obtain a first set of interrogation wavelength/angular measurements; (d) removing the microplate from the holder; (e) re-inserting the microplate back onto the holder; (f) re-scanning the optical beam across the row of the fiducial markings/reference sensors within the microplate to determine a second position of the microplate; (g) determining a position deviation of the microplate comparing the first position and the second position of the microplate; (h) calculating a scan trajectory to take into account the position deviation of the microplate; (i) re-scanning the optical beam using the calculated scan trajectory over the row of biosensors within the microplate to obtain a second set of interrogation wavelength/angular measurements; and (j) comparing the first set of interrogation wavelength/angular measurements and the second set of interrogation wavelength/angular measurements to determine whether or not a biological substance is present or a biomolecular event occurred on one or more of the biosensors within the microplate. An optical interrogation system that is capable of implementing this method is also described herein.

BRIEF DESCRIPTION OF THE DRAWINGS

A more complete understanding of the present invention may be had by reference to the following detailed description when taken in conjunction with the accompanying drawings wherein.

DETAILED DESCRIPTION

Figure 1:
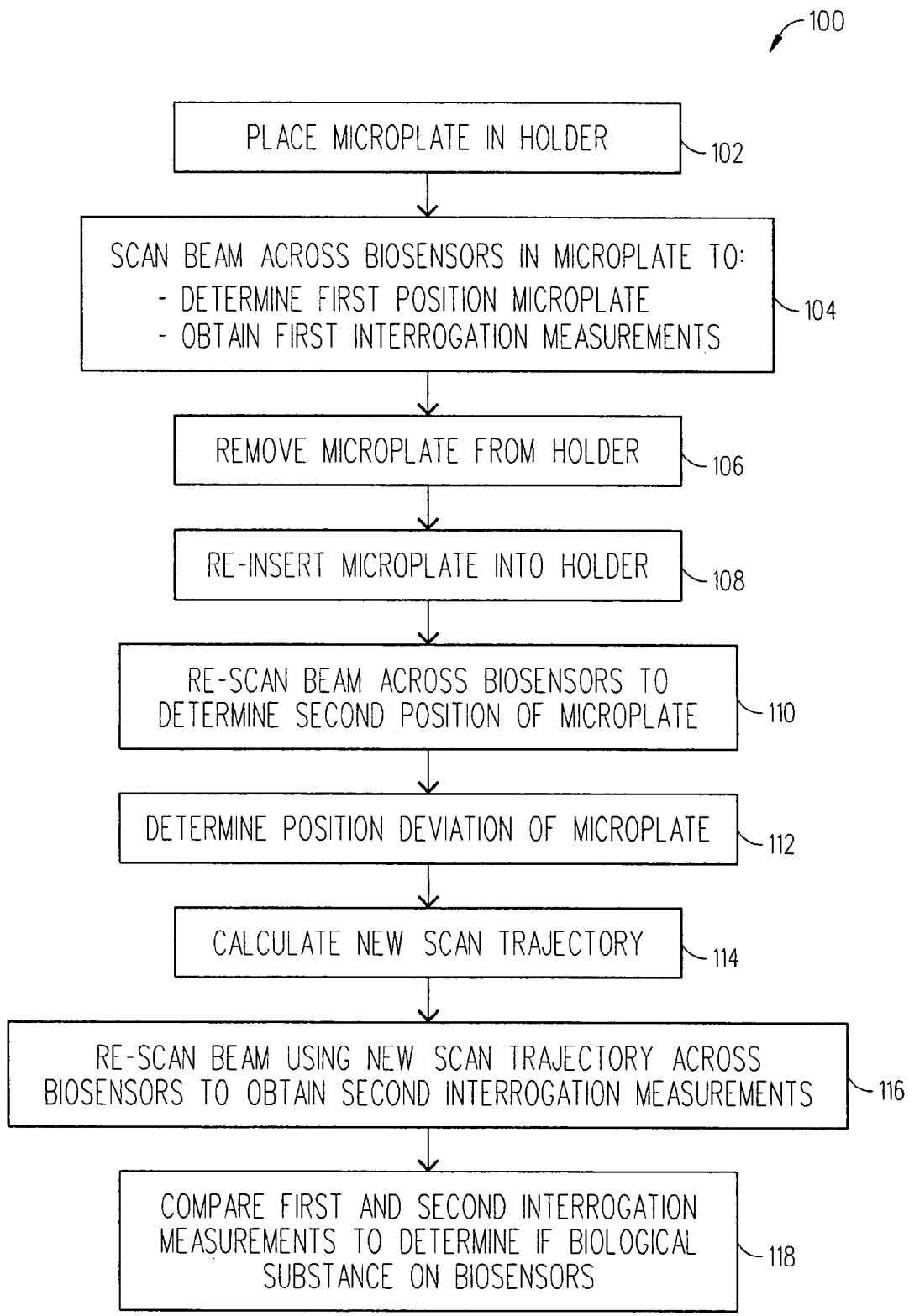
FIGS. 1-26 are drawings used to help explain an optical interrogation system and an interrogation method in accordance with a first embodiment of the present invention.

Referring to FIG. 1, there is a flowchart illustrating the steps of a method 100 for interrogating biosensors which are located within the wells of a microplate in accordance with a first embodiment of the present invention. The method 100 includes the following steps: (a) placing the microplate onto a holder (step 102); (b) scanning an optical beam across a row of the biosensors within the microplate to determine a first position of the microplate and to obtain a first set of interrogation wavelength/angular measurements (step 104) (note: if desired this step can be performed in two separate scanning steps); (c) removing the microplate from the holder (step 106); (d) re-inserting the microplate back onto the holder (step 108); (e) re-scanning the optical beam across the row of the biosensors within the microplate to determine a second position of the microplate (step 110); (f) determining a position deviation of the microplate by comparing the first position and the second position of the microplate (step 112); (g) calculating a scan trajectory to take into account the position deviation of the microplate (step 114); (h) re-scanning the optical beam using the calculated scan trajectory over the row of the biosensors within the microplate to obtain a second set of interrogation wavelength/angular measurements (step 116); and (i) comparing the first set of interrogation wavelength/angular measurements and the second set of interrogation wavelength/angular measurements to determine whether or not a biological substance is present or a biomolecular event occurred on one or more of the biosensors within said microplate (step 118) (note: these results are stored, outputted or presented to a human operator). A detailed discussion about each of the steps associated with method 100 is provided after a brief discussion about an exemplary optical interrogation system 200 which is capable of implementing the steps of method 100 in accordance with one embodiment of the present invention.

Figure 2:
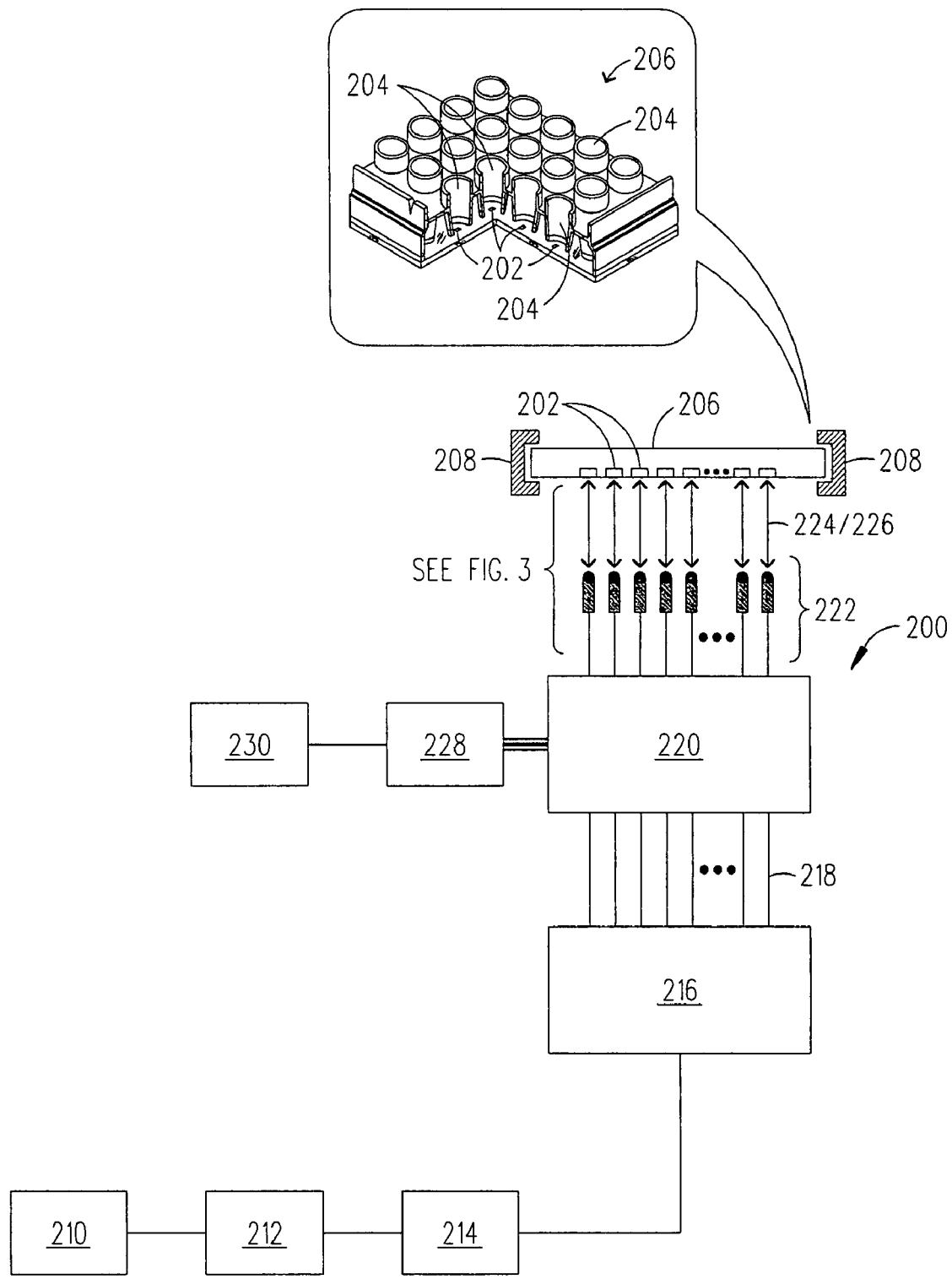

Referring to FIG. 2, there is shown a schematic of an exemplary optical interrogation system 200 which is capable of interrogating biosensors 202 located within the wells 204 of a microplate 206 that is placed on a holder 208 (XY translation stage 208) utilizing the aforementioned method 100 in accordance with the first embodiment of the present invention (note: in the discussion below a 384-well microplate 206 is utilized) The optical interrogation system 200 includes a light source 210 (superluminescent diode (SLD) 210) which is fiber pigtailed and connected to a variable optical attenuator (VOA) 212 that is connected to a polarization scrambler 214. The polarization scrambler 214 outputs a light beam which is split by a 1×16 splitter 216 into 16 individual optical fibers 218. A 1×2 splitter array 220 having 16 channels connects each optical fiber 218 (e.g., single mode fiber 218) to one of 16 fiber microlenses 222 (see FIG. 3). Each fiber microlens 222 (which has a single mode fiber 301) delivers a light beam 224 to a moving biosensor 202 (or static biosensor 202) and also receives a reflected light beam 226. The reflected light beam 226 passes through the 1×2 splitter array 220 and is detected by one of sixteen spectrometers 228. Each spectrometer 228 (optical detection system 228) collects the raw spectral data (interrogation measurements) in the reflected light beam 226 and this raw spectral data is read-out by a personal computer (PC) 230. The PC 230 records the raw spectral data/interrogation measurements as a function of the position of the holder 208 (XY translation stage 208). In addition, the PC 230 analyzes the raw spectral data (interrogation wavelength/angular measurements) which is obtained during steps 104, 110 and 116 to detect and account for any positional misalignment of a re-positioned microplate 206 and interrogate the biosensors 202 in accordance with the first embodiment of the present invention.

Figure 3:
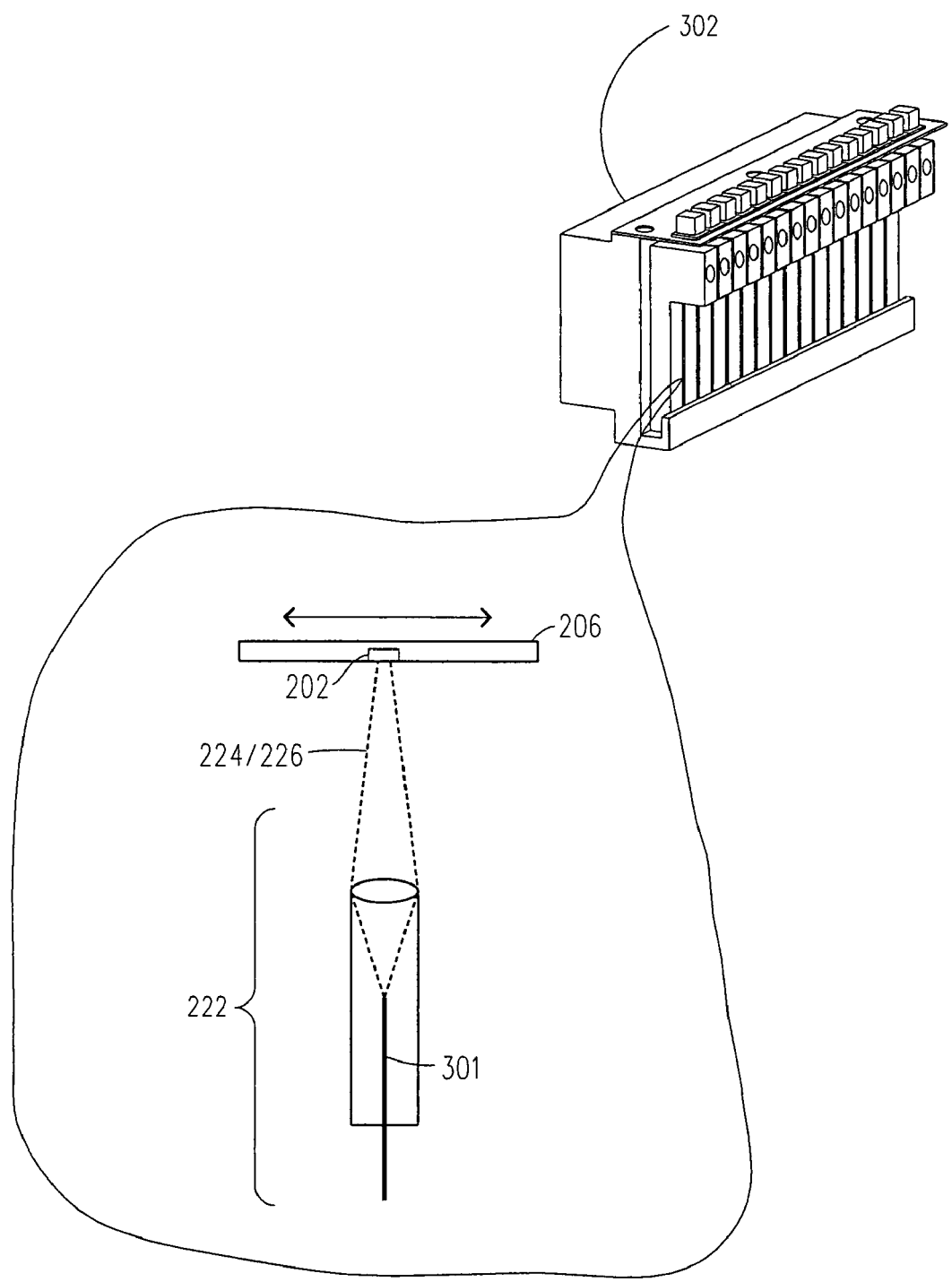
Figure 4:
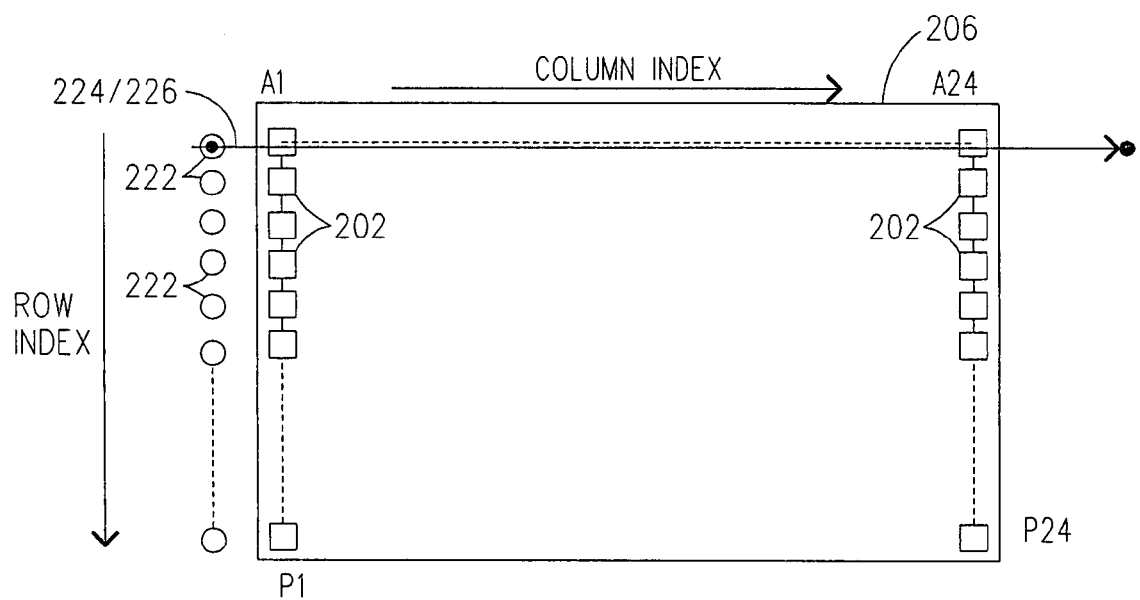

In this exemplary wavelength optical interrogation system 200, a wide spectrum light source 210 is used to illuminate the biosensors 202 and the PC 230 is used to analyze the resonance spectral content of the reflected light beams 226 (note: if desired an angular optical interrogation system could be used to implement method 100). As shown in FIGS. 2-4, the microplate 206 is moved across a fixed optical head 302 which holds 16 fiber microlenses 222 and each fiber microlens 222 emits one optical beam 224 which interrogates the biosensors 202 in one row on the microplate 206 (note: the optical head 302 and one microlens 222 are shown in FIG. 3). The precision X/Y translation stage 208 is used to move the microplate 206 (see FIG. 2). A typical 384 well format microplate 206 is approximately 3 inches in width and 5 inches in length. Hence, to read the entire microplate 206, the X/Y translation stage 208 may move up to 125 mm in distance along the x dimension of the microplate 206, but typically less than 4.5 mm in the y-dimension since 16 lenses 222 are linearly arranged along the y-dimension. In this example, the X/Y translation stage 208 contains an optical encoder that provides pulses for every 200 nm of motion. The PC 230 tracks and records these pulses so that the absolute position of the X/Y translation stage 208 holding the microplate 206 is known at any given time during the interrogation of the biosensors 202 within the microplate 206. Unfortunately, the microplate 206 can move within the mount of the X/Y translation stage 208 because of plate removal/reinsertion events, physical alteration of the microplate 206 during handling steps, thermal expansion, etc . . . and this movement adversely affects the interrogation of the biosensors 202 within the microplate 206. This particular problem is addressed by the present invention.

Figure 5:
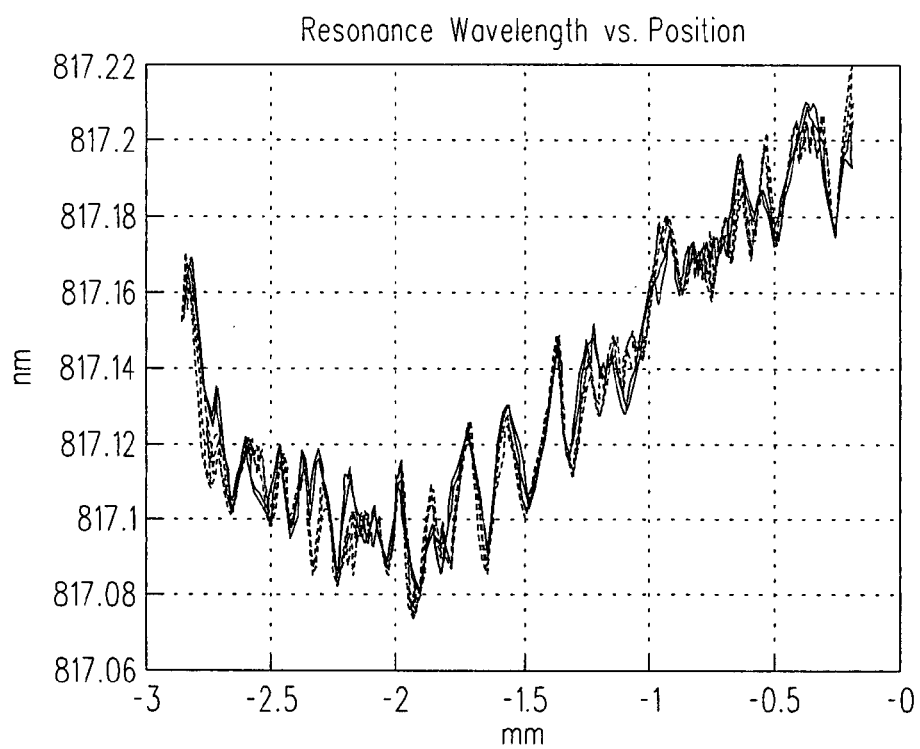
Figure 6:
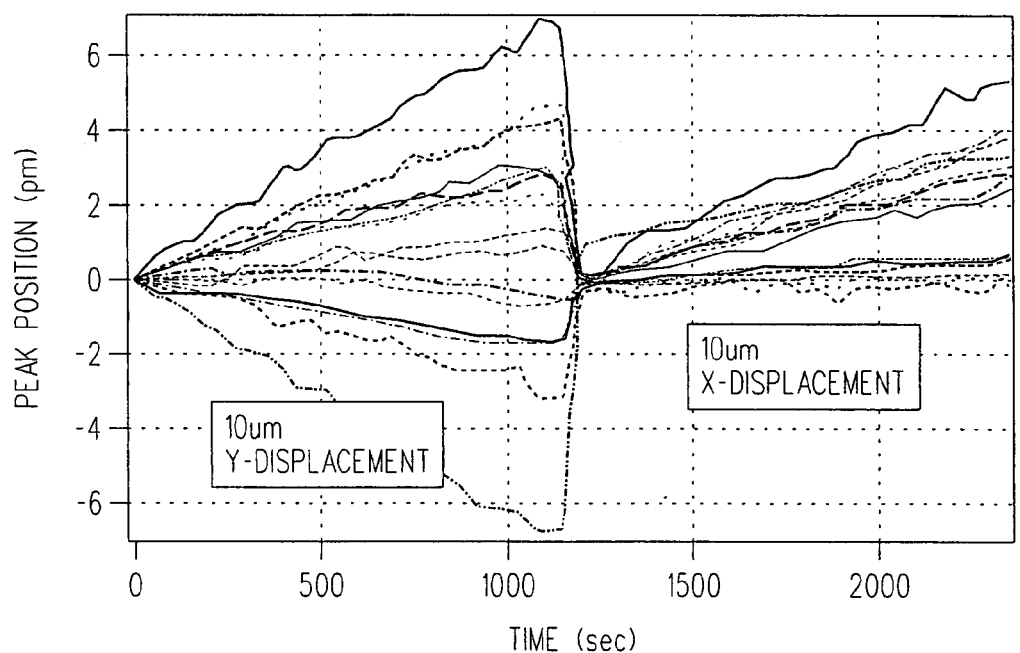
Figure 7:
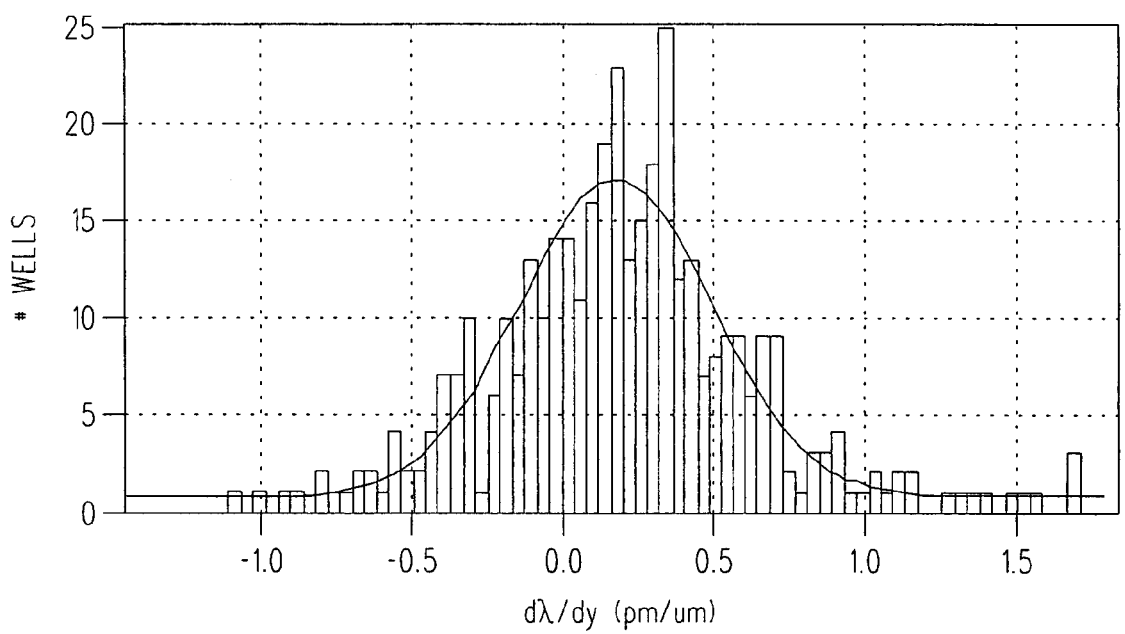

FIG. 5 shows the typical shape of the resonance wavelength of the reflected light beam 226 as a function of position that was obtained when scanning the light beam 224 in one direction across a single 3 mm long biosensor 202. The low and high spatial frequency modulation of the resonance wavelength is generated by non-homogeneities (e.g., local variations of the waveguide thickness) of the biosensor 202. A test has been performed to assess the impact that these non-homogeneities on biosensors 202 have on the reflected light 226 when the biosensors 202 are translated in the y or x direction (see the results in FIGS. 6-8). FIG. 6 shows the wavelength measured for 16 biosensors 202 as the microplate 206 is first displaced in the y-direction by 0-10 microns in 0.5 micron steps, and then displaced in the x-direction by 0-10 microns in 0.5 micron steps. One observes that each biosensor 202 has a completely different sensitivity to displacement. The exact sensitivity of wavelength to a given change in position (dλ/dx or dλ/dy) is determined by the local coating topography on each biosensor 202. This local topography may be influenced by the optical coatings used to create the biosensor 202 itself, or from surface chemistry layers that are used to create inorganic/organic chemistry interfaces, or by immobilized proteins, antibodies, cells, or other chemical or biochemical species on the biosensor 202. Hence, even if a fabrication process is used which creates extremely uniform optical biosensors 202, further modifications of the surface made to alter the biosensor 202 for detecting chemical attachment may cause the surface to become very non-uniform in reflected wavelength. As a result, it has been observed that biosensors 202 may have a somewhat random topography and translation sensitivity relative to other biosensors 202 within the microplate 206. FIG. 7 is a histogram which illustrates the statistical distribution of translation sensitivity of 384 biosensors 202 located within the microplate 206 which was translated in the y direction. If the microplate 206 had completely homogeneous biosensors 202, then this histogram would have had a single large peak, such that some form of referencing could be used to remove wavelength shift artifacts induced by a position shift of the microplate 206. However, the histogram shows that the biosensors 202 exhibited position sensitivities that are variable. These variable position sensitivities have a distribution that can be characterized by using a standard deviation. In this experiment, the standard deviation of the position sensitivities was 0.6 pm/um which means that if one wants to control the noise which is introduced by the positional induced wavelength shifts to 0.1 pm (which may be appropriate for small molecule assays) then the position of the microplate 206 needs to be controlled to be within the range of ~170 nm. This particular accuracy range is possible with the present invention.

Figure 8:
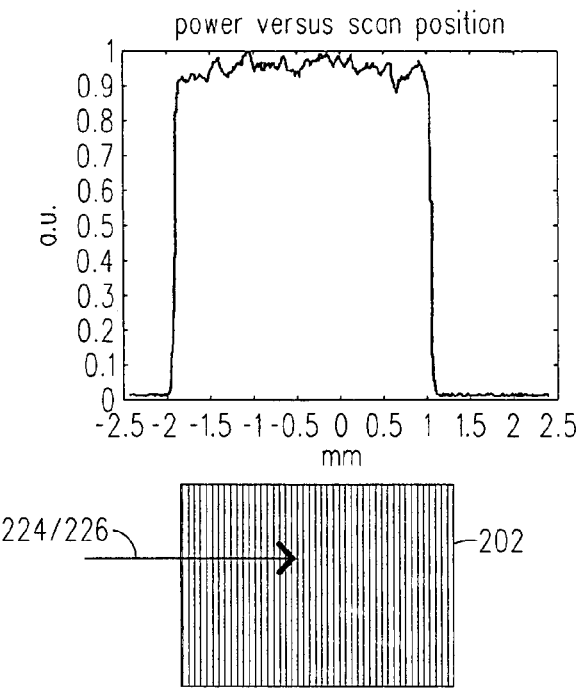

Referring to FIG. 8, this graph illustrates the power vs. position of the reflected light beam 226 as the light beam 224 is scanned across one of the biosensors 202, and as such this information can be used to enable one to locate the edge(s) of the biosensor 202 which in turn enables them to determine the location of the microplate 206 (steps 104 and 110) (see the co-assigned U.S. patent application Ser. No. 11/210,920). The XY location of the biosensor 202 can be determined if the biosensor 202 is scanned in both the X and Y direction or if the biosensor 202 has an angled edge 2502 or a non-responding angled line 2504 formed in the diffraction grating as shown in FIG. 25 (note: recall that the acquisition of the data related to the reflected light beam 226 is synchronized to the encoder on the XY translation stage 208).

Figure 9:
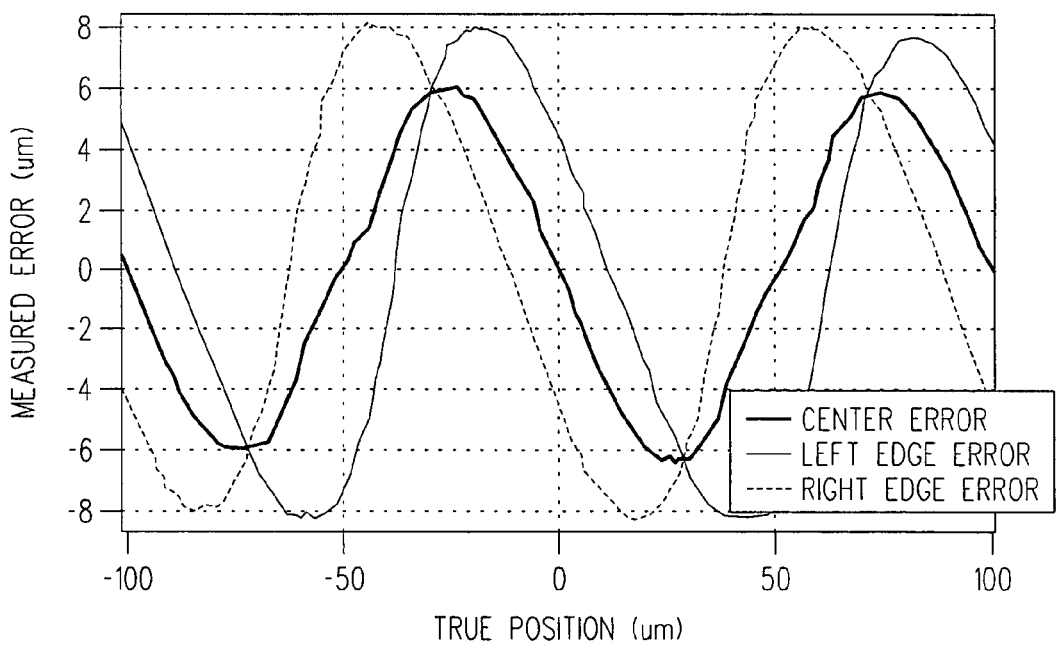
Figure 10:
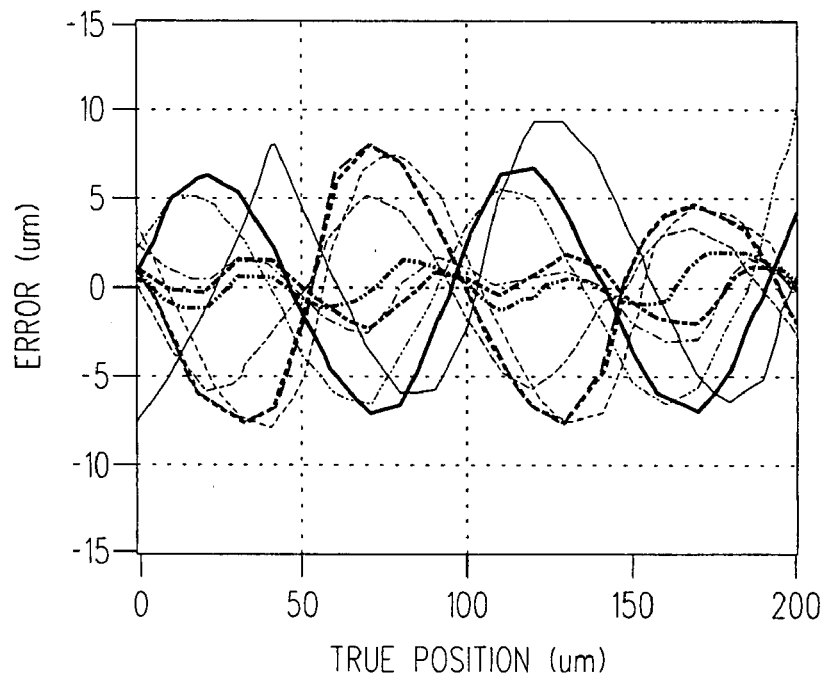
Figure 11:
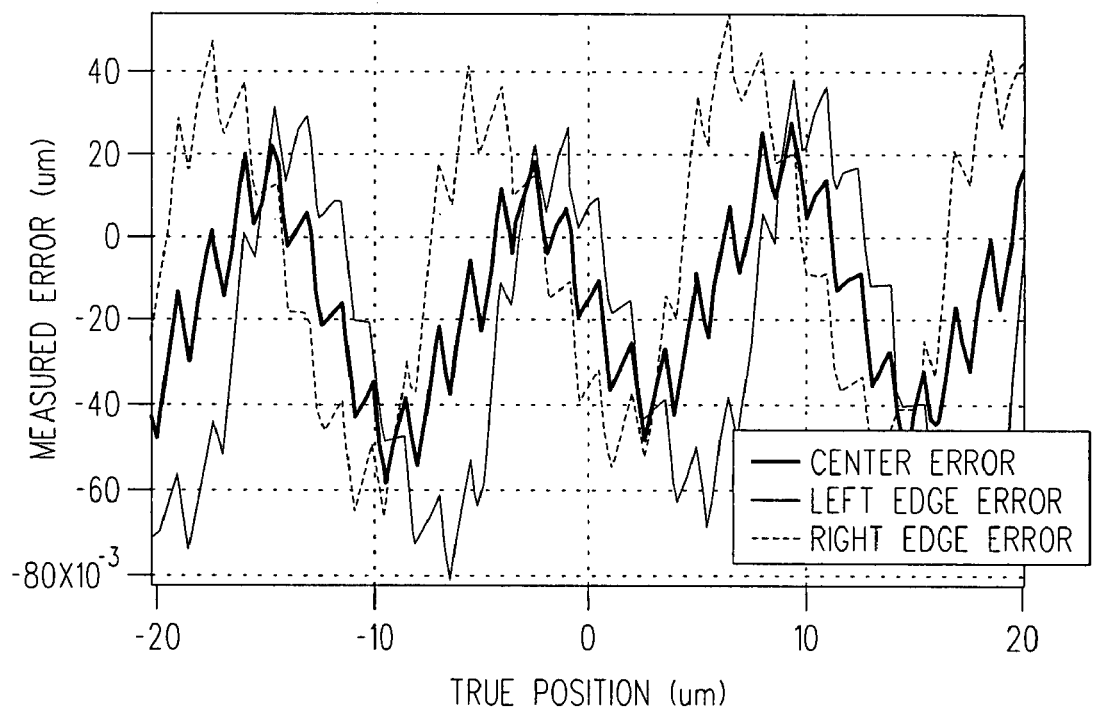
Figure 12A:
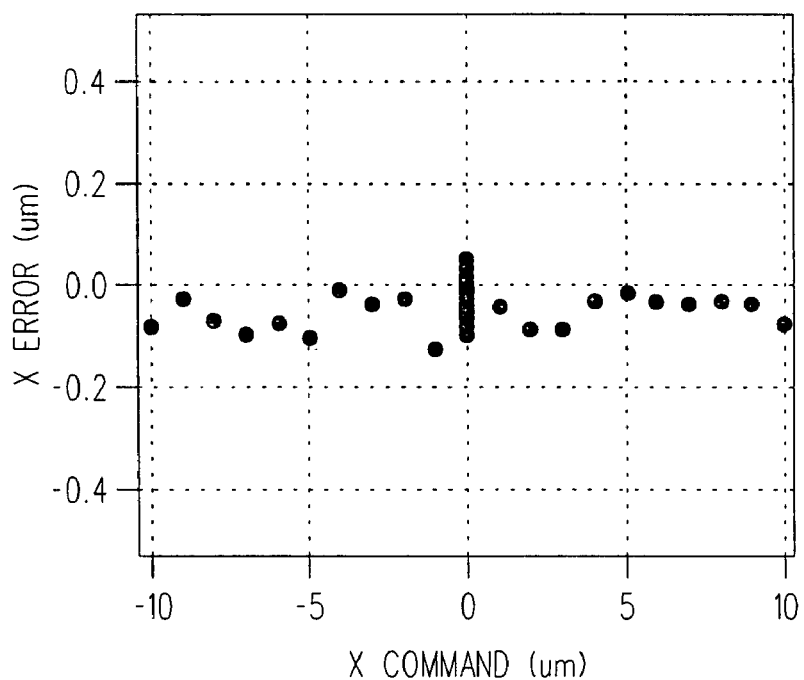
Figure 12B:
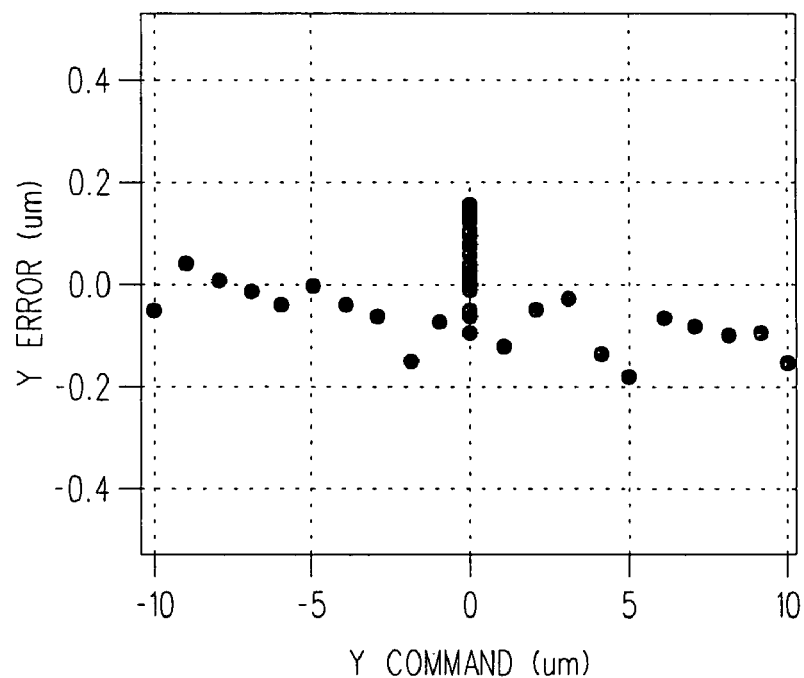

As described in co-assigned U.S. patent application Ser. No. 11/210,920, the PC 230 can determine the position of the microplate 206 by using various edge detection algorithms which include, for example, centroid techniques, derivative techniques, curve fitting techniques, autocorrelation techniques, and edge crossing techniques. However, one issue with all of these edge detection techniques is that if the sampling interval (pixel size) on the spectrometer 228 is too large, then pixelation induced non-linearities may perturb the accuracy of the measurement. This adverse effect of the pixelation induced non-linearities is illustrated in the model shown in FIG. 9 and the experimental data, obtained for various biosensors 202 within a microplate 206, is shown in FIG. 10 (note: the model indicates the error in the estimation of a sensor edge location when the spatial samples were made every 96 µm). As can be seen, the finite spatial pixel (sample) size causes a periodic error in the estimation with a period that is equal to the pixel size. The exact magnitude of this error depends on the exact position, or phase, of the pixel edge relative to the sensor edge. With the 96 µm pixel size used to obtain the data shown in FIG. 9 and FIG. 10, the magnitude of the grating location error is approximately +/−8 um, which is far too large to achieve an ~170 nm repositioning goal. However, the amplitude of this error can be reduced by reducing the pixel size on the spectrometer 218 (see co-assigned U.S. Patent Application Ser. No. 60/781,397). This can be easily accomplished in the aforementioned scanned beam optical system 200. FIG. 11 is a graph that indicates the modeled results when the spatial pixel size is reduced to 12 um (compare to FIGS. 9-10). FIGS. 12A and 12B show the experimental confirmation of this reduced spatial pixel size model, where the data was obtained by using 12 um spatial pixels and the resulting edge position error was a function of known microplate displacements of −10 microns to +10 microns along the x and y axes (note: this reduced spatial size technique could be utilized when performing steps 104, 110 and 116.) As a consequence of reducing the pixel size to 12 um, the grating location error is reduced to <+/−80 nm, which allows the measurement to be accurate enough such that the system can meet the ~170 nm plate repositioning goal.

Figure 13:
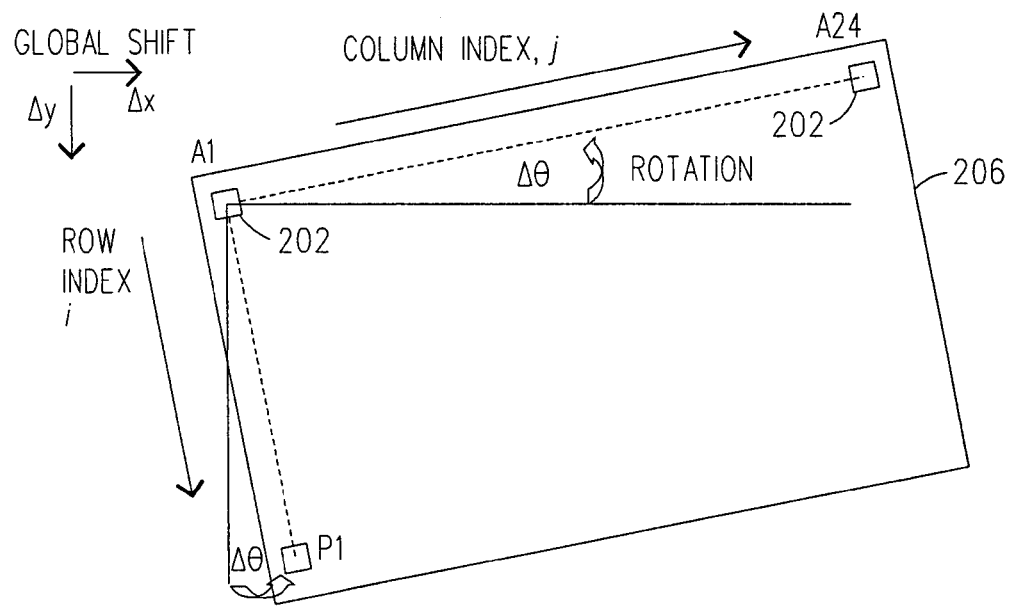

To evaluate where the microplate 206 is relative to the optical beams 224, the microplate 206 is first scanned and the apparent grating positions of the biosensors 202 are measured, to comprise a "before" measurement of position. Then, the microplate 206 is re-scanned and specific spatial regions of the diffraction gratings on the biosensors 202 are integrated, or averaged to produce a first set of interrogation measurements containing wavelength readings (or angular readings) for each biosensor 202 (see FIG. 4) (note: if desired these two scanning steps can be performed in a single scanning operation as discussed in step 104 of method 100). Thereafter, the microplate 206 is removed from and re-inserted back into the XY translation stage 208 (steps 106 and 108). At this point, the microplate 206 is scanned again to measure the position of the biosensors 202 to create an "after" set of position data (step 110). Then, the "before" and "after" position data are compared, and a position deviation is calculated (step 112). If the microplate 206 is taken to behave as a rigid body, then its change in position may be characterized by a global displacement in the x direction, Δx, a global displacement in the y-direction, Δy, and a rotation, Δθ as shown in FIG. 13. The position deviation is used to calculate a new scan path (or trajectory) across the microplate 206 (step 114). Then, this new scan trajectory is used to scan and record a second set of interrogation measurements for the biosensors 202 while assuring that the original spatial regions of the diffraction gratings on the biosensors 202 that were interrogated to produce the first set of interrogation measurements are again used to produce this new set of interrogation measurements (step 116). A detailed discussion is provided next to explain how the position deviation information could be used to calculate a new scan path (or trajectory correction) across the microplate 206 (step 114).

Figure 14:
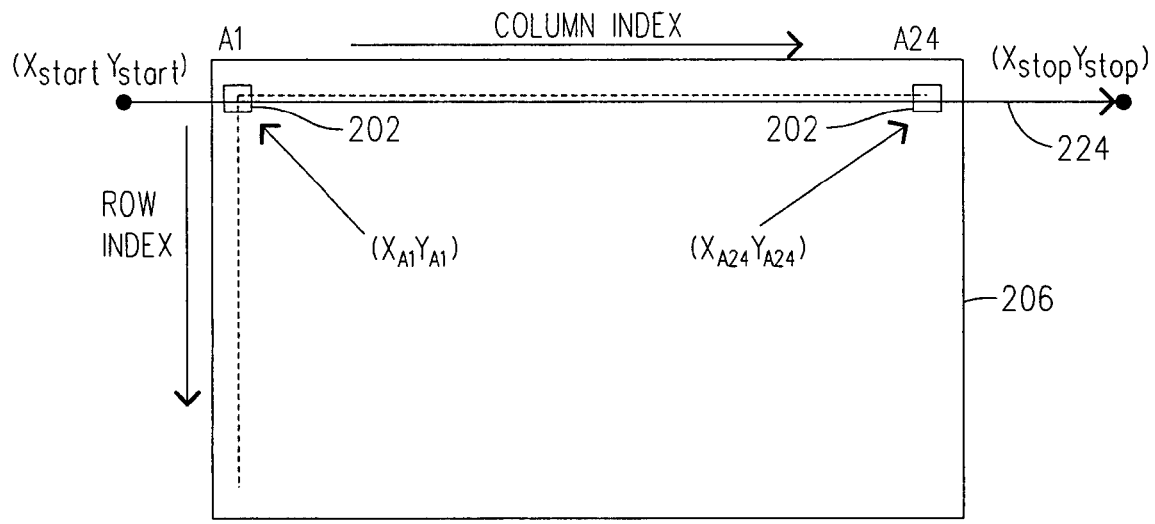
Figure 15:
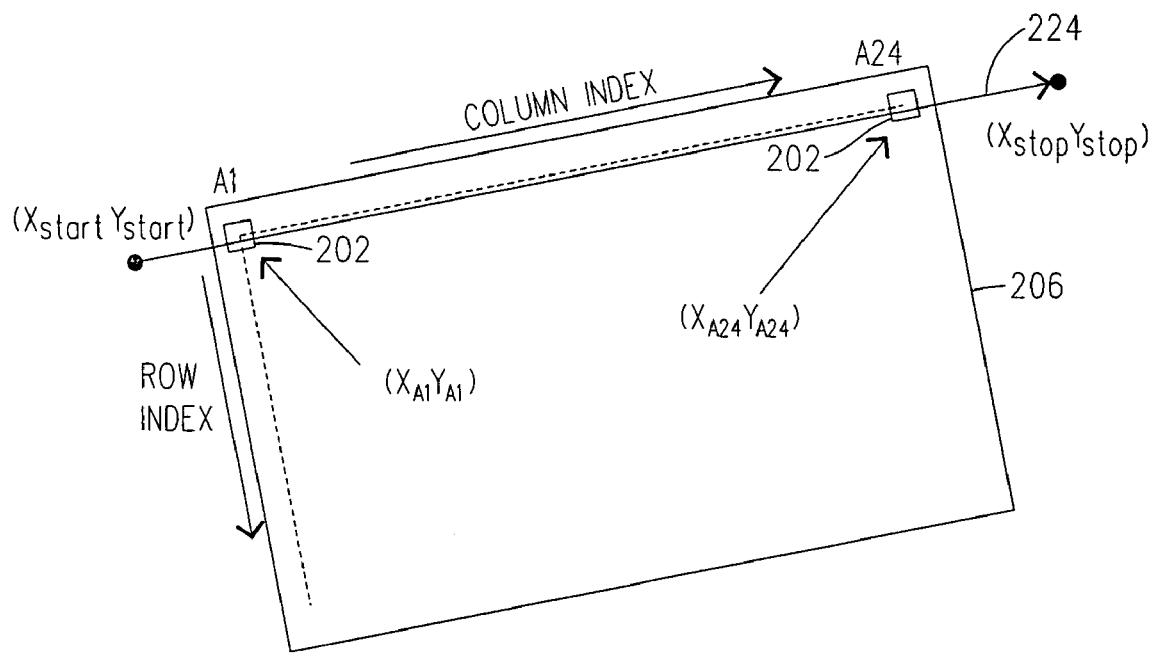

Once the position deviation data for the microplate 206 is measured, a new scan trajectory (or scan correction) is calculated before performing the "last" scanning step to interrogate the biosensors 202 on the microplate 206 (steps 112, 114 and 116). For a static microplate 206 and a series of scanned optical beams 224, or for a scanned microplate 206 and a series of static optical beams 224, a linear trajectory is used to define the new scan path that each optical beam 224 is to take across each row of biosensors 202. Referring to FIG. 14, to define this linear scan trajectory, a start scan point ($x_{start}$, $y_{start}$) and an end scan point ($x_{stop}$, $y_{stop}$) need to be specified. Since, all the optical beams 224 are rigidly fixed together (as is depicted in FIGS. 3 and 4), the start scan point and stop scan point for any one beam 224 effectively defines trajectories for all 16 beams 224. In the case shown in FIG. 14, the path of the row A optical beam 224 is used to illustrate the beam movement across the microplate 206, the other 15 beams 224 traverse parallel trajectories but offset by multiples of approximately 4.5 mm in the row (y) direction. Once the new linear scan trajectory is defined then the optical beam 224 will traverse the same portion of each biosensor 202 during each of the interrogation steps 104 and 116. Such a new scan trajectory is shown in FIG. 15. An example of how this new linear scan trajectory could be calculated in accordance with the present invention is discussed next.

An exemplary technique that can be used to find the linear scan trajectory is to measure where the position of biosensor A1 appears ($x_{A1}, y_{A1}$) and where the position of biosensor A24 appears ($x_{A24}, y_{A24}$), and use these points as the start scan point ($x_{start}, y_{start}$) and end scan point ($x_{stop}, y_{stop}$). However, in practice it is desirable to over scan the biosensors A1 and A24 by some distance to ensure the entire surfaces of biosensors A1 and A24 are measured and to ensure that acceleration/deceleration of the requirements of the motion stage used for the scanning step 116 are satisfied. This technique is illustrated in FIG. 14 (which depicts an unperturbed microplate 206) and FIG. 15 (which depicts a perturbed microplate 206).

A preferred strategy when determining the linear scan trajectory is to use biosensor/grating displacements ($\Delta x_{ij}, \Delta y_{ij}$) instead of absolute biosensor/grating positions to evaluate the position of the microplate 206. Here (i,j) denote the (row, column) indices of a well. The reason to use displacements rather than absolute positions is that each row of lenses 222 may have a unique pointing error or misalignment—i.e. the optical and mechanical axes of each lens 222 may not be perfectly aligned, and hence each optical beam 224 may not be separated from the others by the exact pitch of the biosensors 202—although this pointing error will be constant in time (see FIG. 2). One can remove the impact of this pointing error, and the difficulty in accounting for it within the calculations by using displacements rather than absolute positions. For a rigid body translation and rotation of the microplate 206, one can write the change in position of each biosensor 202 as a sum of a global translation displacement and a rotation displacement of the microplate 206 as follows (equation nos. 1 and 2):

$$\Delta x_{ij} \approx \Delta\theta \cdot (y_{ij}) + \langle \Delta x \rangle \qquad 1$$

and $$\Delta y_{ij} \approx \Delta\theta \cdot (x_{ij}) + \langle \Delta y \rangle \qquad 2$$

As is illustrated in FIG. 13, $\Delta x$ and $\Delta y$ are the global x and y displacements that the microplate 206 has undergone, and $\Delta\theta$ is the angular rotation of the microplate 206. Here $x_{ij}$ and $y_{ij}$ represent the absolute x or y locations of a given biosensor/grating 202 relative to biosensor/grating A1. Thus the displacement of each biosensor/grating 202 arises from a purely translational component ($\Delta x$ and $\Delta y$) and a purely rotational component ($\Delta\theta * x_{ij}$ and $\Delta\theta * y_{ij}$). Therefore, as one can see from equation 1 and 2, if one experimentally measures the values of the $\Delta x_{ij}$'s and $\Delta y_{ij}$'s (steps 104 and 110), then the two equations may be solved to obtain the global x-displacement ($\langle \Delta x \rangle$) of the microplate 206, the global y-displacement ($\langle \Delta y \rangle$) of the microplate 206 and the rotation ($\langle \Delta\theta \rangle$) of the microplate 206.

The following procedure describes in more detail one possible way of solving equations 1 and 2. If the microplate 206 moves as a rigid body with only a small rotation, then all the wells within the same row should have the same x-shift, and any variation in x-shift should arise simply from measurement noise. Hence, after obtaining the ($\Delta x_{ij}, \Delta y_{ij}$) of all measured biosensors 202 on the microplate 206, the global x-shift $\langle \Delta x \rangle$ and the plate rotation $\Delta\theta$ may be calculated by fitting a line to the following (equation no. 3):

$$\langle \Delta x \rangle_i \approx \Delta\theta \cdot (y_i) + \langle \Delta x \rangle \qquad 3$$

Figure 16:
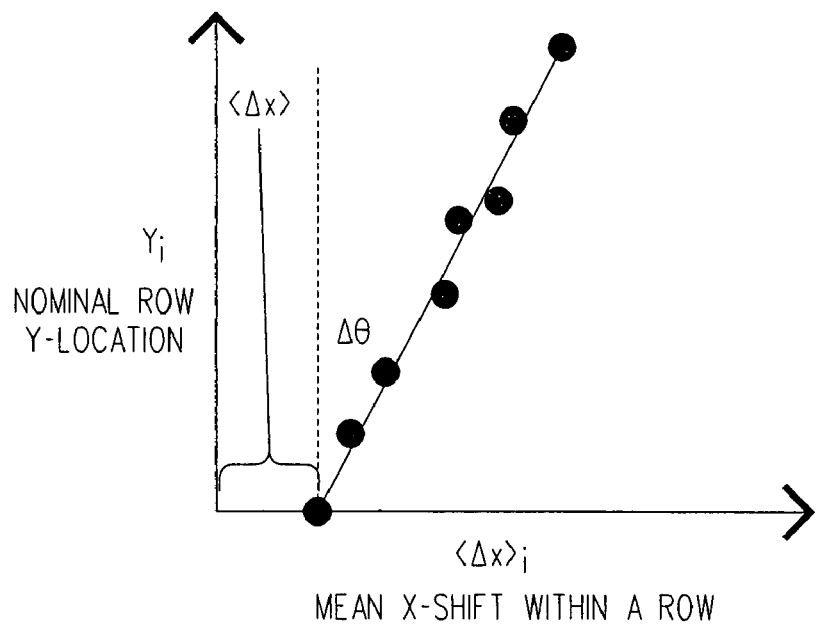

Here $\langle \Delta x \rangle_i$ represent the common (or average) of the x-shift of all 24 biosensors 202 within that particular row. As can be seen, equation no. 3 indicates that each row of biosensors 202 will have a slightly different x-displacement due to the term containing the row dependent component of the plate rotation $\Delta\theta$. The calculation of the global x-shift and plate rotation $\Delta\theta$ of the microplate 206 by using individual x-shifts of each biosensor 202 is graphically illustrated in FIG. 16. The offset of this line is the global x shift, $\langle \Delta x \rangle$. And, the slope of this line (1/slope in the plot) is the plate rotation, $\Delta\theta$.

Likewise, the global y-shift $\langle \Delta y \rangle$ may be calculated by fitting a line to (equation no. 4):

$$\langle \Delta y \rangle_j \approx \Delta\theta \cdot (x_j) + \langle \Delta y \rangle \qquad 4$$

Figure 17:
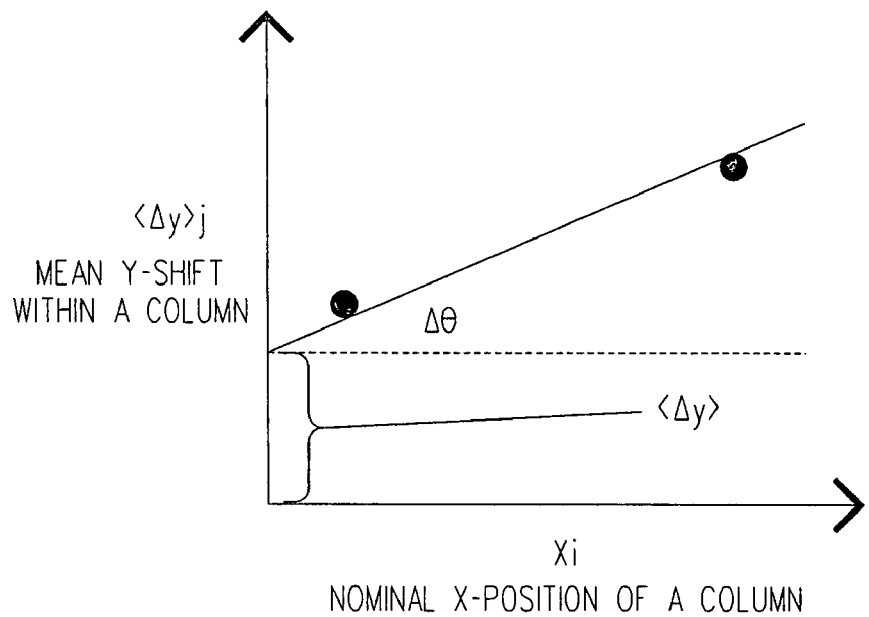
Figure 18:
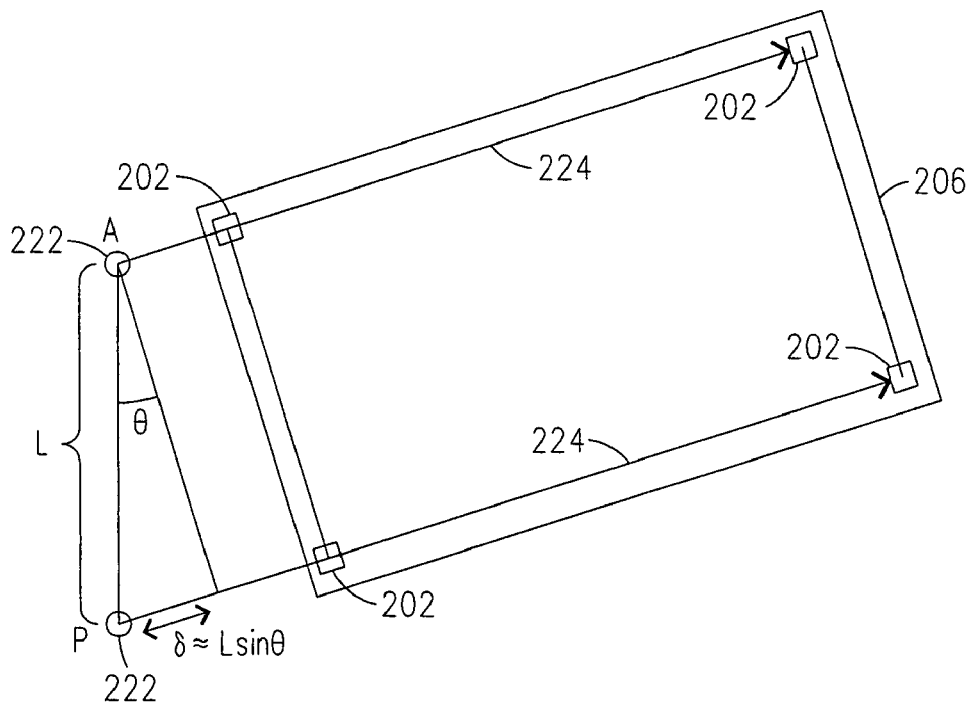

Here $\langle \Delta y \rangle_j$ represents the common (or average) of the x-shift of all 24 biosensors 202 within a particular column. The calculation of the global y-shift of the microplate 206 by using individual y-shifts of each biosensor 202 is graphically illustrated in FIG. 17. As can be seen, equation no. 4 indicates that each column of biosensors 202 is going to have a slightly different y-displacement which is due to the global shift $\langle \Delta y \rangle$ and the column dependent component of the plate rotation $\Delta\theta$. The offset of this line is the global y shift, $\langle \Delta y \rangle$. Finally, the rotation of the microplate 206 may be calculated by obtaining the slope $\Delta\theta$ from either the line fit to the x-shift data or the y-shift data The above analysis ensures that each optical beam 224 traverses the same physical area on the biosensors 202 during the two scanning steps 104 and 116. However, an additional complication in using the new scan trajectory arises if the microplate 206 undergoes a rotation. In this situation, a time (or position, or phase delay) is induced on the optical channels for each row of biosensors 202 that varies from one channel/row to another channel/row. FIG. 18 illustrates the phase delay ($\delta$) between the different rows of biosensors 202 on the microplate 206. As can be seen, even though lens A and lens P traverse the centers of the biosensors 202 on their respective rows, there is a physical delay in time or distance between when they each first "see" their respective biosensors 202. The amount of this time delay ($\delta$) in physical scan distance is equal to L sin $\theta$, where $\theta$ is the rotation angle, or the slope, which was calculated in equation nos. 1-4.

Figure 19:
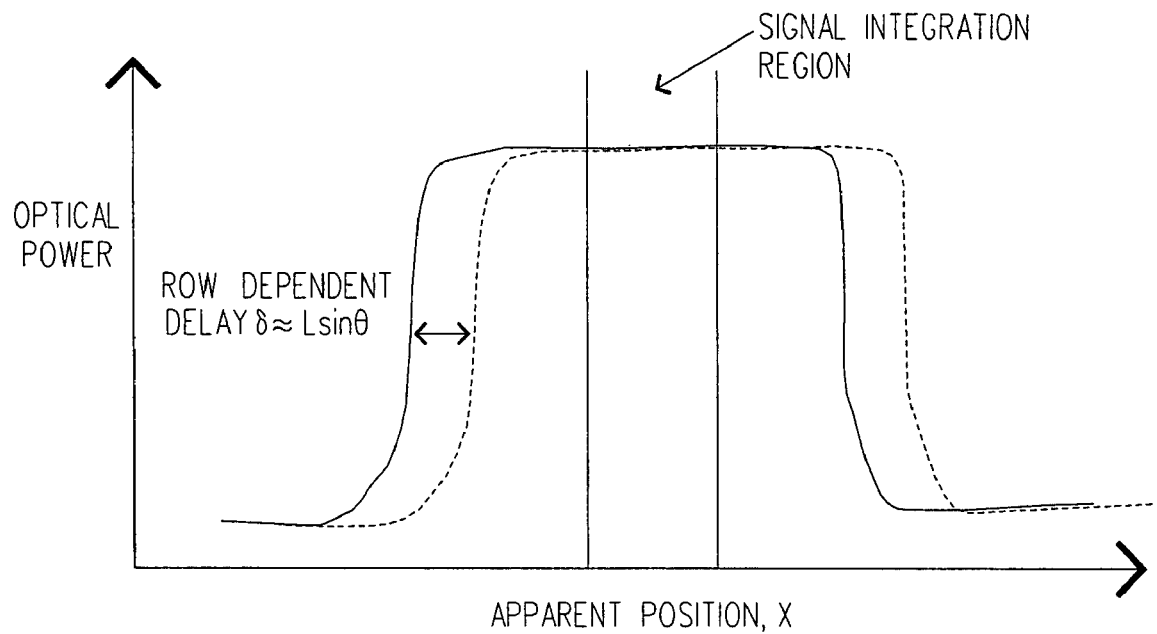

The effect that a plate rotation induced phase delay has on the apparent position of a biosensor 202 (or fiducial edge) has been graphically illustrated in FIG. 19. As can be appreciated, if there is a phase delay, then for a given optical beam 202, the biosensors/gratings 202 may appear shifted in apparent position along the scan direction, and the optical channels may not necessarily integrate the desired regions of the biosensors 202 within the rotated microplate 206. Since the pixel size of the scan may be large (for example, 12 um cited above) compared to the accuracy with which one wants to compensate (for example, <170 nm cited above), then digitally adjusting the integration regions to compensate for the delay after the data is acquired may be too imprecise (i.e. 12 um pixels are coarse compared to the desired 170 nm precision). One manner in which this problem can be addressed is if the XY translation mount 208 has an actuator which can adjust the rotation of the microplate 206, then the rotation calculated above may be used to determine how to drive this actuator to correct the angle of the microplate 206. However, if no rotation actuator is used, then another technique needs to be used to compensate for the phase delay induced by the rotation of the microplate 206. For instance, one technique may involve introducing a precision time or position delay as to when each individual spectrometer 228 is to be triggered to acquire its respective scan data (see FIG. 2). Since optical encoders for motion stages allow for very precise position triggering (much better than the <170 nm positioning requirement), it is possible to achieve such a delay to sufficient precision. To calculate the time or position delays for each individual row of biosensors 202 on the microplate 206, one can use the following (equation no. 5):

$$delay_i = \Delta\theta \cdot (y_i) \qquad 5$$

(note: this equation is derived from the row-dependent component of the x-shift used above in equation no. 3).

An additional consideration which could be taken into account when determining the microplate position deviation, is that thermal or other environmental changes may cause the microplate itself or the position encoder used on the XY translation stage 208 to expand or contract, thus changing the apparent distance between the biosensors 202, i.e. the sensor pitch, on the microplate 206 (note: other causes which can make a microplate 206 expand or contract include for example water absorption which would make the microplate swell if it had a plastic bottom plate). In particular, a thermal change may occur if the XY translation stage 208 is cold for one measurement and then warm for another measurement or vice-versa. Likewise, the microplate 206 itself may thermally expand or contract which would create errors in the measurements. In either case, even if the correct scan trajectory is calculated and implemented, the regions of integration for each biosensor 202 will be slightly altered by this thermal dilation effect. Ideally, if the microplate 206 acts as a rigid body, then the x-shift for all biosensors 202 within a row should be the same between the two measurements. However, if there is a pitch change that occurs between the two measurements, then one will observe a column-dependent variation in the x-shift of the biosensors 202. Hence we should modify equation 1 to be:

$$\Delta x_{ij} \approx \langle \Delta x \rangle + \Delta\theta \cdot (y_{ij}) + \Delta\phi \cdot (x_{ij}) \qquad 6$$

It should be noted that we did not modify equation 2, because, for the particular interrogation system described herein, which has the linear array of 16 optical beams 224 as shown in FIG. 4, each optical beam 224 traverses more than 100 mm in the x-direction, but only ~3 mm in the y-direction for a plate measurement. Hence the pitch change is not a significant consideration in the y-direction, since any thermally induced dilation of the microplate 206 or optical encoder will be ~33× smaller in total magnitude. For a common glass expansion coefficient of ~5 parts per million per deg C, and a 0.5 deg C. change in system temperature, the x-dimension of the microplate 206 would change by ~250 nm, whereas the y-dimension would change by only 8 nm (note: this assumes the microplate 206 has a glass bottom plate). The former is of concern for the ~170 nm microplate positioning requirements, however that latter is not. Hence, it is acceptable to neglect the dilation in the y-dimension. However, it should be appreciated that if a system were designed such that a more lengthy scan in the y-direction was used to evaluate the plate position, or if an even more accurate position correction were desired, then a similar pitch change term could be incorporated into equation 2.

Figure 20:
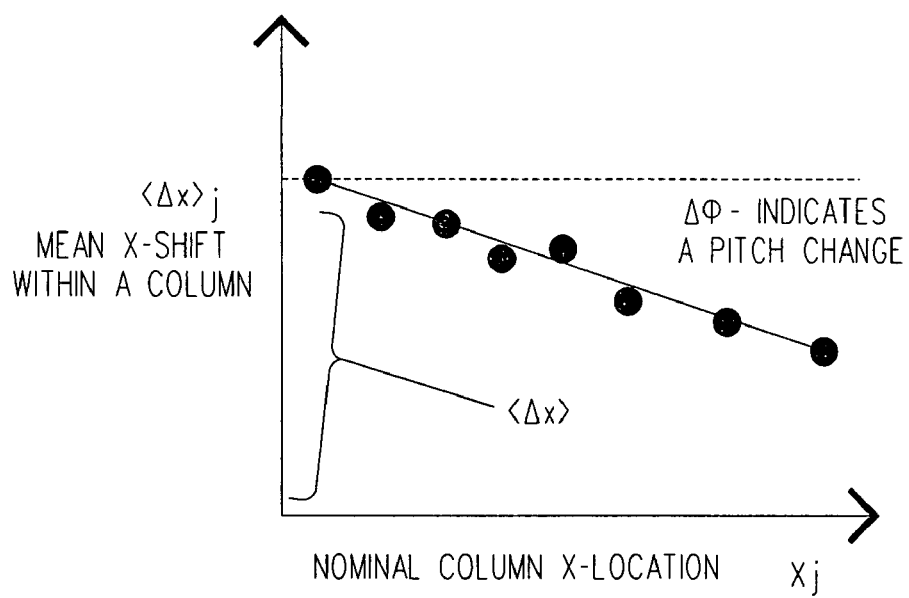

Thus, from equation 6 it can be see that if one plots the mean x-shift for each column (an average of 16 or more data points) vs. the nominal column x-location then this plot will have a slope if there is a pitch change, and no slope if the pitch remained constant between the two measurements. This is illustrated in FIG. 20. The pitch change is the slope of this line, $\Delta\phi$, where a negative slope indicates the microplate 206 has undergone an apparent contraction and a positive slope indicates that the microplate 206 has undergone an apparent expansion (note: the offset of this line on the y-axis is the global x shift, $\langle\Delta x\rangle$). Of course, this may not be due to just microplate 206 expansion/contraction, but could also be due to expansion/contraction of the position encoder on the XY translation stage 208.

After these position deviation parameters: $\langle\Delta x\rangle$, $\langle\Delta y\rangle$, $\Delta\theta$, $delay_i$ for each channel, and the fractional pitch change $\Delta\phi$ are calculated then these parameters are used to determine the subsequent new scan trajectory of the microplate 206 (step 114). From these parameters, various error statistics may be calculated, to determine if a new scan trajectory is sufficiently accurate, or if iteration would be required to improve the positioning of the microplate 206. An example statistic is given by (equation no. 7):

$$Shift_{stat} = \sqrt{(\Delta x_{worstcorner})^2 + (\Delta y_{worstcorner})^2} \qquad 7$$

where $$\Delta x_{ij} \approx \Delta\theta \cdot (y_{ij}) + \langle\Delta x\rangle + \Delta\phi \cdot (x_{ij} - x_{start})$$

$$\Delta y_{ij} \approx \Delta\theta \cdot (x_{ij}) + \langle\Delta y\rangle$$

This particular equation represents the worst vector displacement of the four corner biosensors 206 (A1, P1, A24, P24) on the microplate 206. In this case, the displacement is calculated by knowing $\langle\Delta x\rangle$ and $\langle\Delta y\rangle$, along with knowing the plate rotation $\Delta\theta$ and the pitch error $\Delta\phi$. The calculated displacement represents the worst displacement error on the microplate 206 and assumes a shift and rotation, and a thermal dilation of the microplate 206 and/or the stage encoder in the scan direction.

Figure 21:
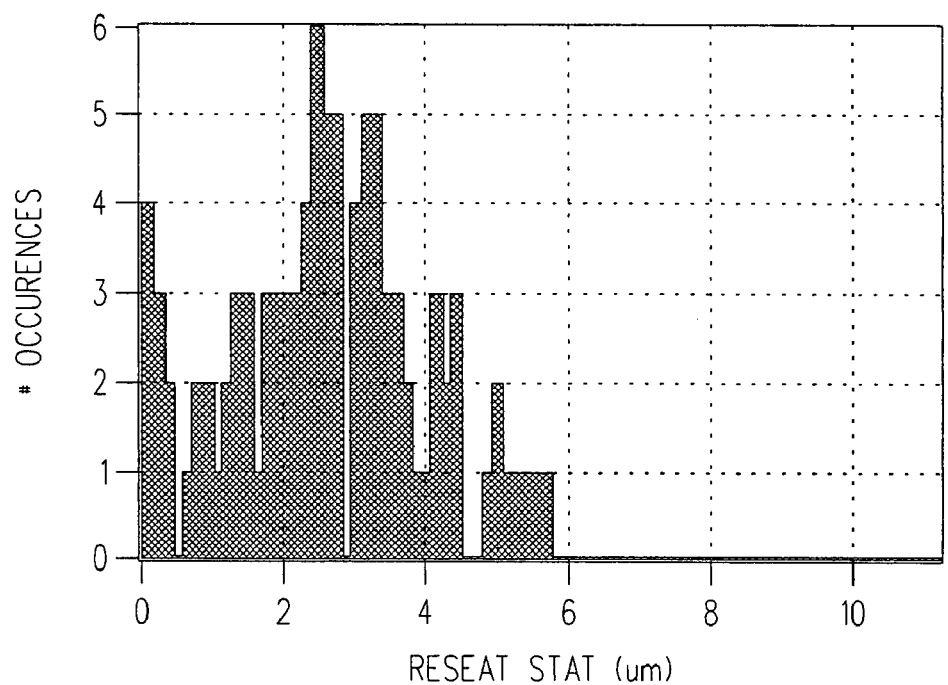
Figure 22:
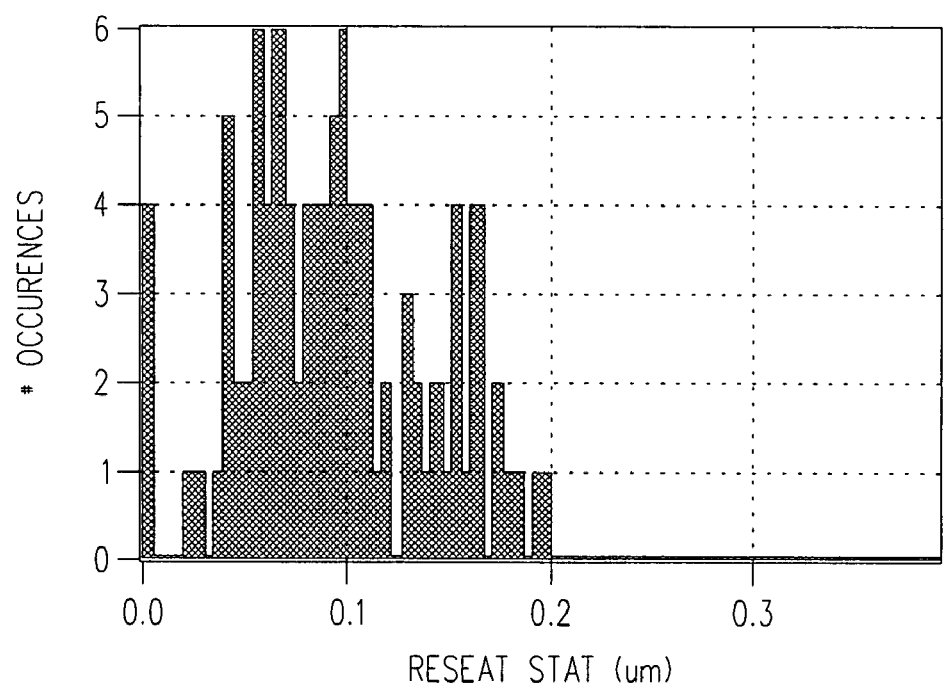

To test the accuracy of the above described techniques, the positions of several microplates 206 have been measured. Data was taken both with and without active position correction. The results, shown in the form of a histogram of position error, are provided in FIG. 21 (no active microplate positioning) and FIG. 22 (active microplate positioning). Without any active microplate position correction, removal/reinsertion events of the microplate 206 caused global shifts and rotations in the position of the microplate 206 within the mounting apparatus of the XY translation stage 208. However, when these movements are measured by the above described techniques, and corrected, the subsequent position deviations of the microplate 200 are kept below 200 nm.

Figure 23A:
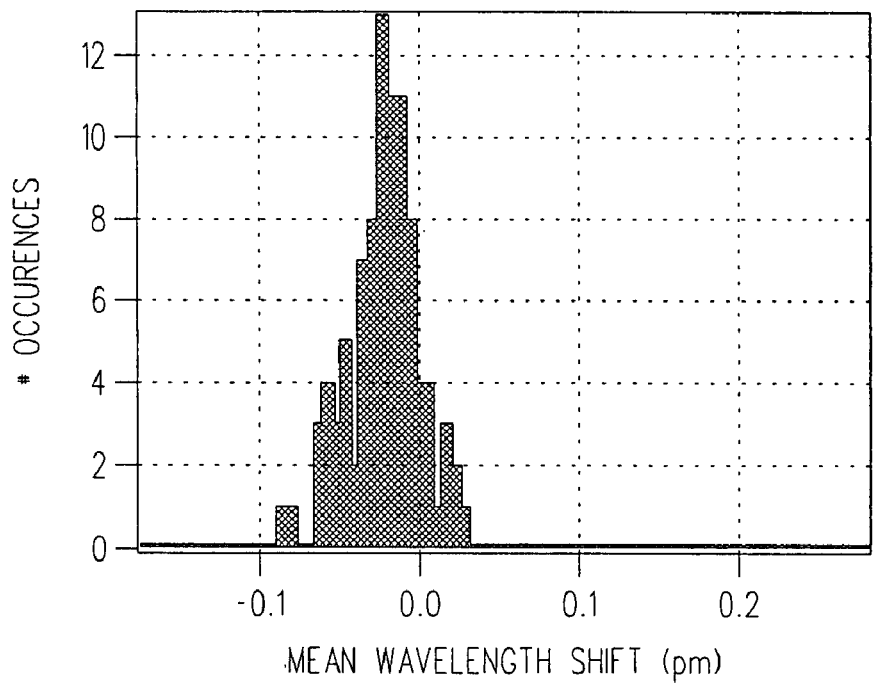
Figure 23B:
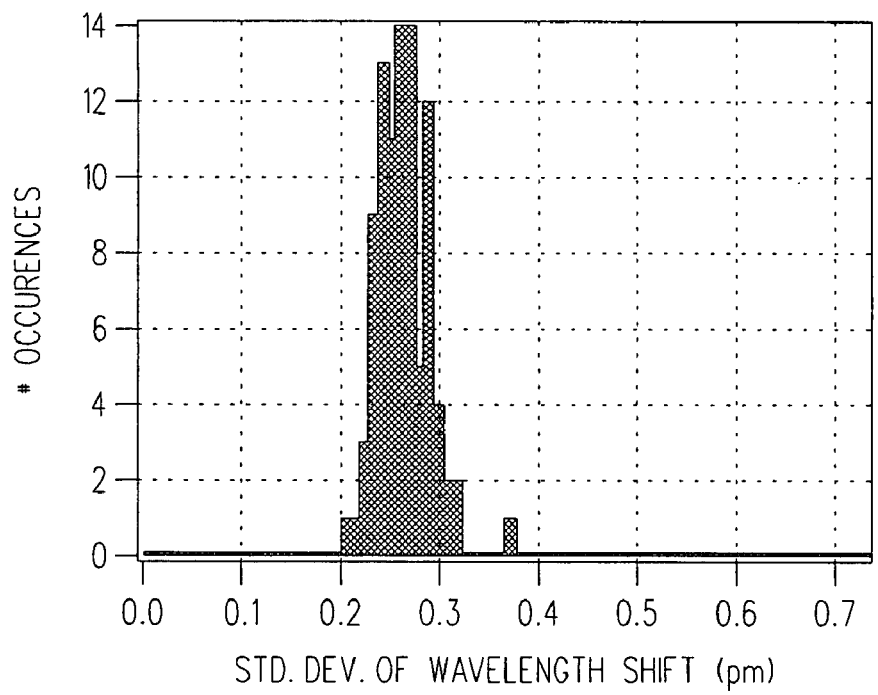
Figure 23C:
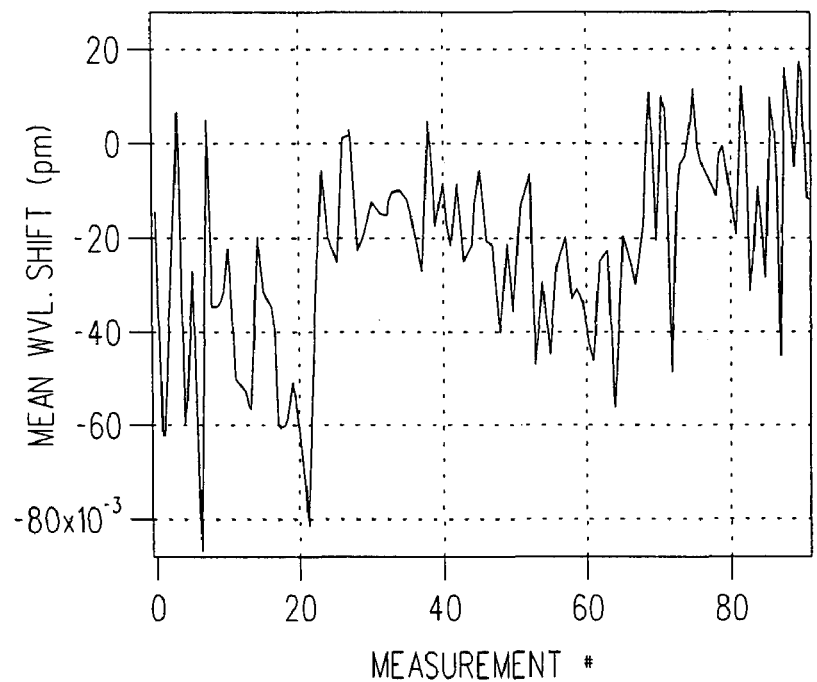
Figure 23D:
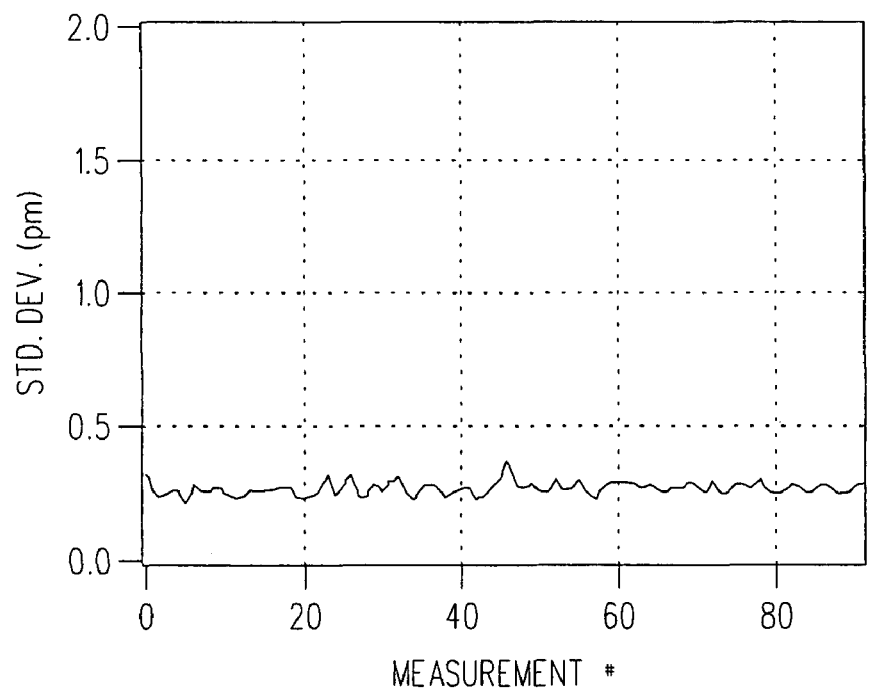

Additionally, FIGS. 23A-23D document that, as a consequence of this active plate positioning technique, the wavelength shifts induced by the microplate removal/reinsertion events can be kept small. FIG. 23A shows a histogram of the mean value of the wavelength shift of all 384 wells in a microplate 206 for 92 plate removal/reinsertion events. FIG. 23B shows a histogram of the standard deviation of the wavelength shifts for 384 wells in the microplate 206 for the same removal/reinsertion events. FIGS. 23C and 23D illustrate the same microplate removal/reinsertion events but with the mean wavelength shift and standard deviation plotted as function of event number. As FIGS. 23A-23D help illustrate, when characterizing the wavelength shift induced by a plate removal/reinsertion event, an appropriate figure of merit is not the mean wavelength shift seen across the 384 sensors, since, if there happened to be any average shift across the microplate 206 from a removal/reinsertion event, then it could be easily removed by use of a dedicated reference sensor or sensors. Instead the spread in wavelength shifts, or standard deviation, induced is a more appropriate figure of merit. A spread in the wavelength shifts across various wells/biosensors 202 represents a "noise" induced by plate removal events that can not be distinguished from a well/biosensor 202 dependent biochemical change at the surface of the microplate 296. Hence minimizing the spread or standard deviation of wavelength shifts induced by a removal/reinsertion event is of paramount importance. Without active position control, position shifts of ~ microns induce a wavelength shift noise (standard deviation) of ~ picometers. Even larger displacements (>few microns) and hence higher noise levels (>few picometers) can be induced if the microplate 206 is physically damaged between reads by the plate handling equipment, or if there is significant thermal expansion or contraction of the microplate 206. However, as FIG. 23B shows, with active position control reducing the sensor displacements to <200 nm, one observes typical standard deviations in the wavelength shift of 0.2-0.4 pm. This noise level means that small molecule binding events are detectable, even with plate removal occurring between reads.

Figure 24:
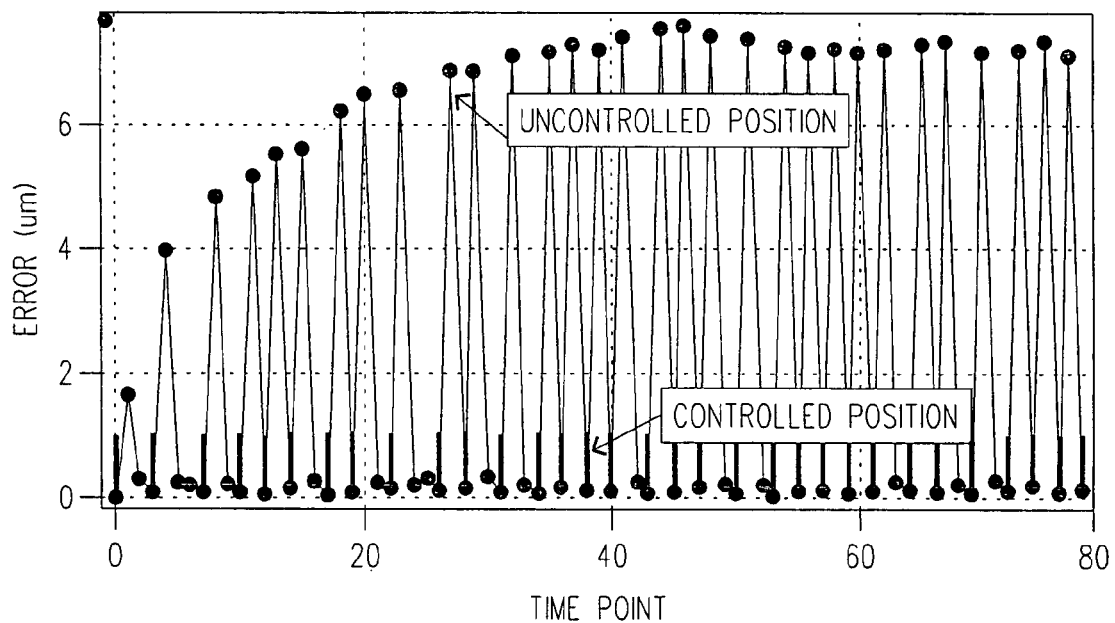

In addition to being used to actively compensate for the discrete removal/reinsertion events of the microplate 206, the position measurement can also be used to help compensate for gradual events. Such changes frequently occur if a microplate 206 is not at a stable temperature, causing it to expand/contract and shift within the mount of the XY translation stage 208. FIG. 24 shows such a time dependent tracking using the active plate positioning technique, where it is illustrated how for a given microplate 206 thermal changes can slowly move and rotate the microplate 206 within the XY translation stage 208 (see the thin lines associated with the "uncontrolled position" label). However, the active plate positioning technique of the present invention can be used to adjust the microplate 206 from its thermally perturbed position back to the original position, keeping the resulting position error for any biosensor 202 below 200 nm (see the thick lines associated with the "controlled position" label). In this case, the position of the microplate 206 would be measured and corrected every minute (or other time period).

Figure 25A:
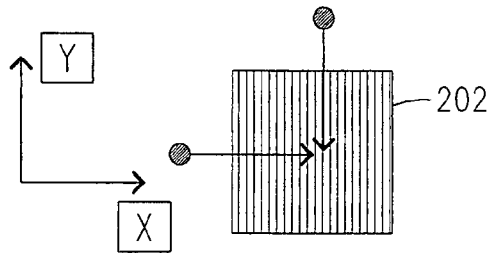
Figure 25B:
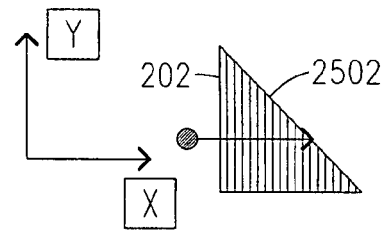
Figure 25C:
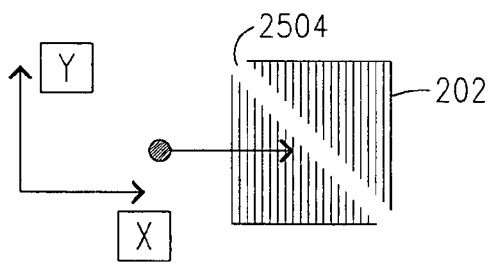
Figure 25D:
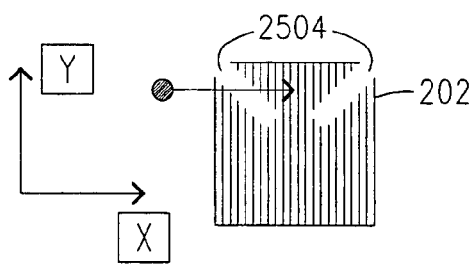

As discussed above, the XY location of the biosensor 202 (and by default the position of the microplate 206) can be determined if the biosensor 202 (which has a square shaped diffraction grating) is scanned in both an X and Y direction as shown in FIG. 25A. Alternatively, the XY location of the biosensor 202 (and by default the position of the microplate 206) can be determined by using a single X direction scan if the biosensor 202 has an angled edge 2502 or a non-responding angled line 2504 formed in the diffraction grating as shown in the examples of FIGS. 25B-25D (see the co-assigned U.S. patent application Ser. No. 11/210,920). The use of biosensors 202 which have an angled edge 2502 or a non-responding angled line 2504 formed in the diffraction grating has several advantages:

1. Since a single scan can be used to accommodate both XY measurements, the measurement cycle may be made faster. That way rapid position feedback may be applied, which allows for higher measurement throughput and improved ability to correct positions in the microplate 206 that evolve with time, such as those induced by changes in the temperature of the microplate 206 itself and/or the XY translation stage 208.

Figure 26:
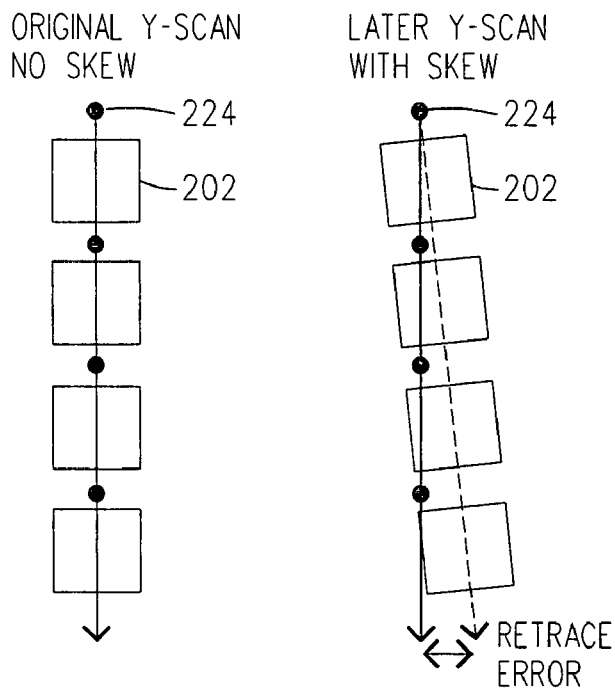

2. In the presence of microplate rotation, and if there is no separate rotation actuator on the XY translation stage 208, then for the 16 optical beam system described herein, the location of the biosensors 202 which are traversed by an optical beam in a separate y-measurement will become distorted. This problem can be explained by referring to FIG. 26 where it can be seen on the right side of drawing where if the microplate 206 is rotated (skewed) then an optical beam 224 scanned in the y-direction will not traverse the original position measurement path, with the amount of error being proportional to the amount of plate rotation ($\Delta\theta$). In practice, since the width of a typical microplate 206 is ~75 mm, and the amount of rotation can be ~100 uRad this can lead to beam position shifts relative to the biosensors 202 of as much as ~7.5 microns, and thus may cause a degradation in the control (position measurement) signal for large plate rotations. However, if a single x-scan is used to scan biosensors 202 which have angled edges 2502 or non-responding lines 2504, then no y-scan would be needed. In this way, the effects of microplate rotation can be properly removed and this particular measurement error could be eliminated.

Figure 27:
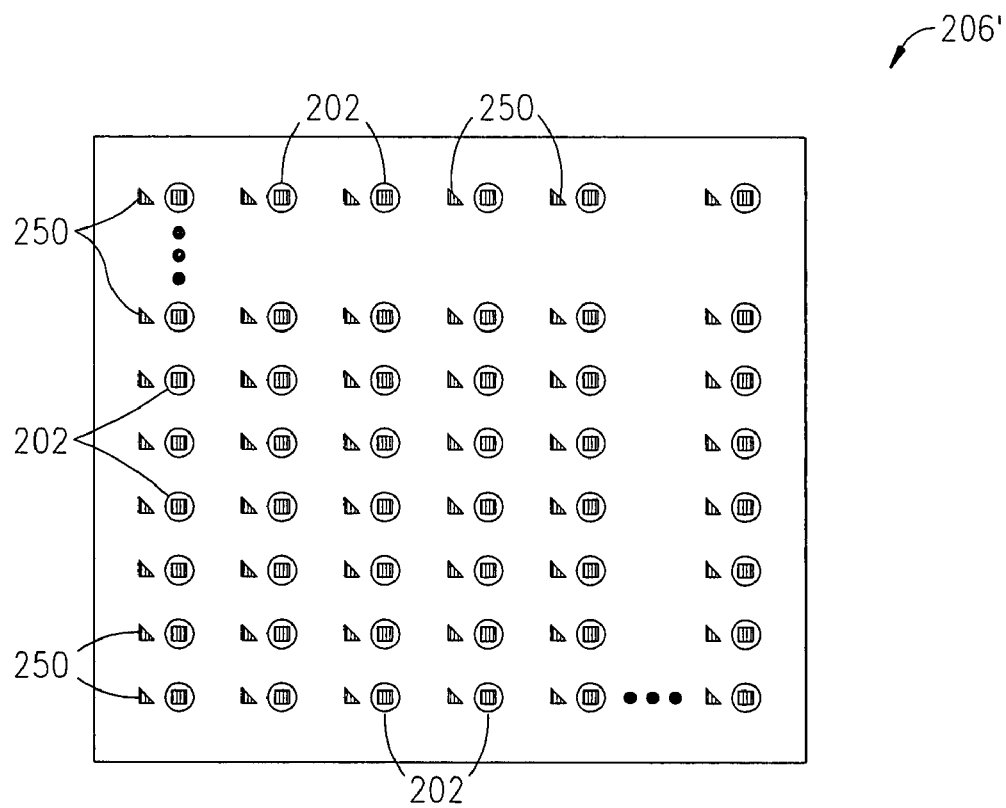
FIGS. 27-28 are drawings used to help explain an optical interrogation system and an interrogation method in accordance with a second embodiment of the present invention.

In a different embodiment discussed below with respect to FIGS. 27-28, one may also use a microplate 206' that incorporates both fiducial markings 250 (reference sensors 250) and the aforementioned sample biosensors 202 (see the co-assigned U.S. patent application Ser. No. 11/210,920). The reference sensors 250 do not need to have angled edges (or non-responsive fiducial lines) but they would preferably have these for the same reasons described above with respect to FIGS. 25 and 26. If desired, the reference sensors 250 could be placed outside the wells of the microplate 206' so that they would be protected from being exposed to chemical agents used in the surface chemistry, the target immobilization, or the assay processes. In addition, the reference sensors 250 could be covered by an epoxy, or covered by some portion of the microplate 206' to help shield them from dust and debris. Basically, the reference sensors 250 should be protected so they are not damaged or altered during the taking of measurements, which could lead to a change in their edges, and hence an error in their perceived positions. Moreover, a consideration in the design of these separate reference sensors 250 is that they should have a similar reflectivity and wavelength as the sample biosensors 202. This helps to ensure that the same scan of the optical beam 224, without any optical power adjustment, may be used to interrogate both the reference sensors 250 and the sample biosensors 202.

Figure 28:
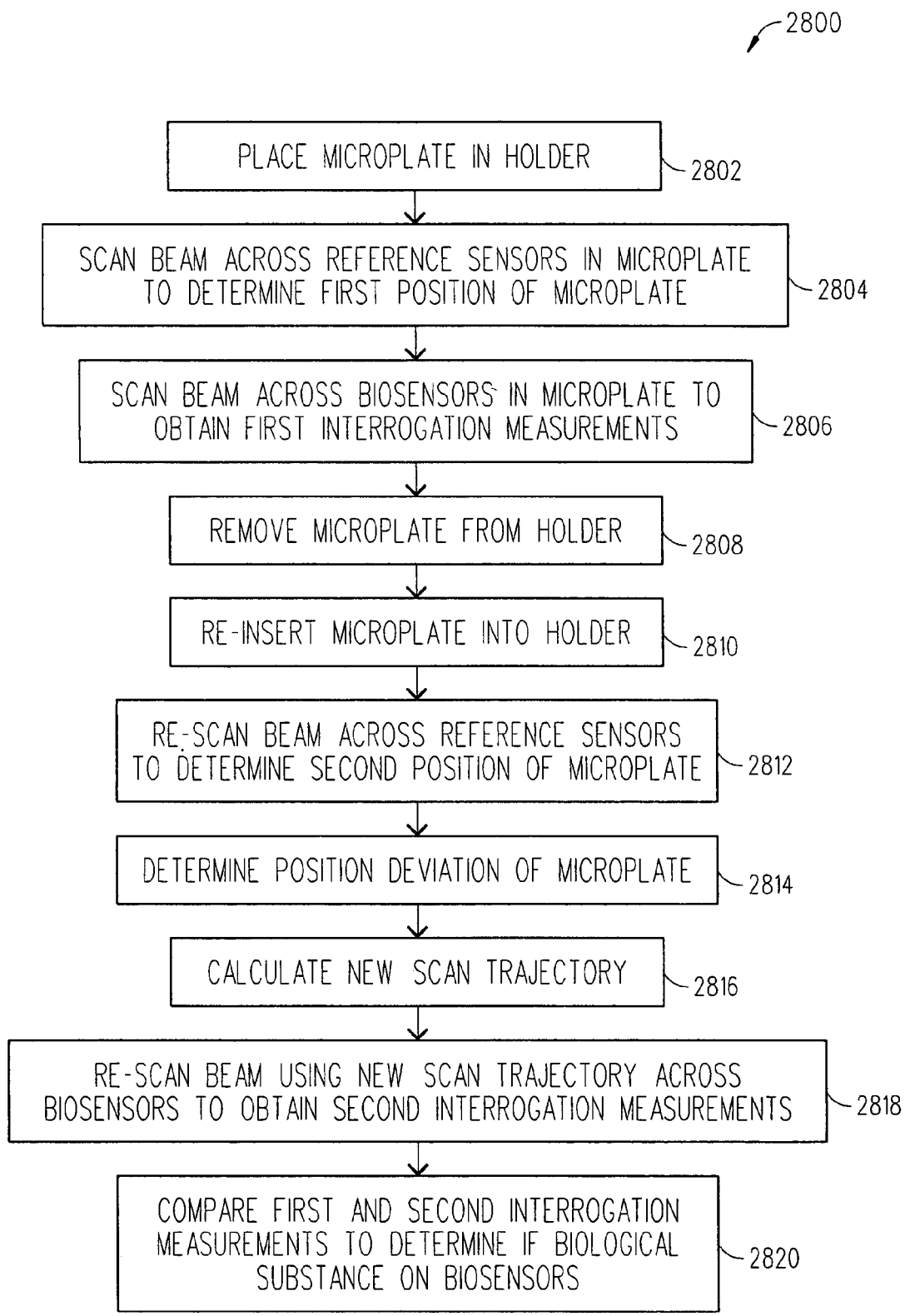

If this type of microplate 206' (which includes both reference biosensors 250 and sample biosensors 202) is utilized, then the following interrogation method 2800 can be performed in accordance with a second embodiment of the present invention (see FIG. 28). The method 2800 includes the following steps: (a) placing the microplate 206' onto a holder (step 2802); (b) scanning an optical beam across a row of fiducial markings/reference sensors 250 within the microplate 206' to determine a first position of the microplate 206' (step 2804); (c) scanning the optical beam across a row of the biosensors 202 within the microplate 206' to obtain a first set of interrogation wavelength/angular measurements (step 2806); (d) removing the microplate 206' from the holder (step 2808); (e) re-inserting the microplate 206' back onto the holder (step 2810); (f) re-scanning the optical beam across the row of the fiducial markings/reference sensors 250 within the microplate 206' to determine a second position of said microplate 206' (step 2812); (g) determining a position deviation of the microplate 206' by comparing the first position and the second position of the microplate 206' (step 2814); (h) calculating a scan trajectory to take into account the position deviation of the microplate (step 2816); (i) re-scanning the optical beam using the calculated scan trajectory over the row of biosensors 202 within the microplate 206' to obtain a second set of interrogation wavelength/angular measurements (step 2818); and (j) comparing the first set of interrogation wavelength/angular measurements and the second set of interrogation wavelength/angular measurements to determine whether or not a biological substance is present or a biomolecular event occurred on one or more of the biosensors 202 located within the microplate 206' (step 2820) (note: these results are stored, outputted or presented to a human operator). The exemplary optical interrogation system 200 can be used to perform this particular method 2800 of the present invention.

It should be noted that in both embodiments of the present invention the same optical beam 224 should be used to perform both the interrogation measurements and the position (fiducial) measurements. The same optical beams 224 should be used because if mechanical motion of the optical beams 224 occurs relative to the microplate 206 and 206', then this relative motion can be calibrated out by the fiducial measurement. Again, this mechanical motion of the optical beams 224 could occur because of the thermal expansion or contraction of the XY holder 208 (or microplate 206 and 206') and/or the reinsertion process of the microplate 206 and 206'. However, if a separate position/fiducial optical measurement system was used then this particular advantage would be lost. For instance, if a separate camera was used to image the reference sensors/fiducials/angled non-responding lines during the position measurement process to determine the position of the microplate 206 and 206'. Then, if relative motion is assumed to occur between the camera and the optical beams, between the camera and the microplate 206 and 206', and between the optical beams and the microplate 206 and 206'. The latter would not be "seen" by the camera measurement of the reference sensors/fiducials/angled non-responding lines, and hence could not be corrected. Thus, it is inherently advantageous to use the same optical beams 224 that perform the reflected interrogation measurements to perform the position (fiducial) measurements.

Furthermore, it should be noted that the drawings herein, were presented based on the assumption that the biosensors 202 are spectrally interrogated. This means that the biosensors 202 are interrogated at a fixed incidence angle with a broad spectral source and that a wavelength is detected in the reflected beams 226. The source is then a broad spectral source and the detector is a wavelength sensitive detector such as a spectrometer. However, it should be appreciated that the present invention can also be extended to an angular interrogation approach where the biosensors 202 would be interrogated with monochromatic light at different angles and then a resonant angle would be detected in the reflected beams 226.

Figure 29:
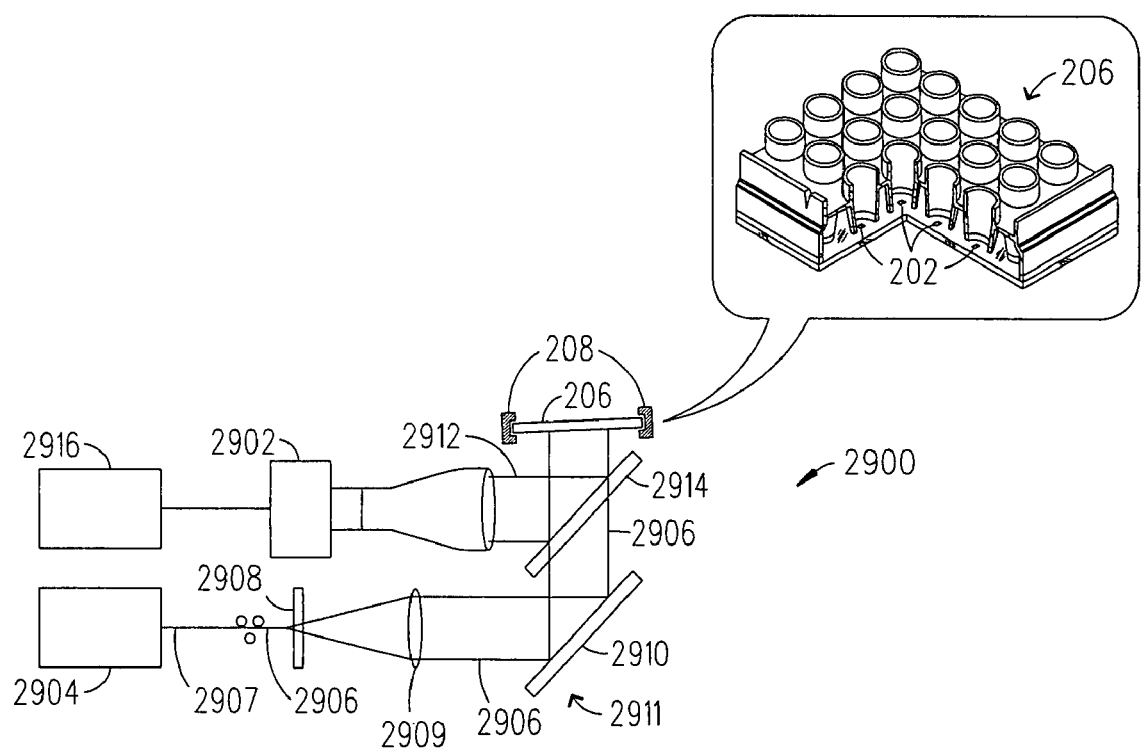
FIG. 29 is a drawing used to help explain an optical interrogation system and an interrogation method in accordance with a third embodiment of the present invention.

It should be noted that scanning allows an image of the biosensors 102 to be made by assembling the sequentially acquired reflected wavelength and power data from the scanned biosensors 102. However, it should be noted that there are configurations of the present invention that do not need to use scanning to measure the position, re-position and/or interrogate the biosensors 202. One exemplary non-scanning system is a vision system 2900 which is shown and discussed below with respect to FIG. 29. Basically, the vision system 2900 would create an image of the biosensor(s) 202, the optical beams 224, and/or the fiducials using a position sensitive detector 2902 (e.g., CCD camera 2902, optical detection system 2902). In particular, the exemplary vision system 2900 as shown has a tunable laser 2904 that emits a light beam 2906 into an optical fiber 2907 such that the light beam 2906 can be outputted and collimated by lenses 2908 and 2909 and then reflected by a mirror 2910 to illuminate the bottom of the microplate 206 (note: components 2904, 2907, 2908, 2909 and 2910 effectively form an imaging system 2911). The exemplary vision system 2900 also includes the camera 2902 which receives a light beam 2912 from a beam splitter 2914 that was reflected from the bottom of the microplate 206. In addition, the exemplary vision system 2900 includes a computer 2916 (or other type of processor 2916) which receives the image from the camera 2902 and measures both the locations of the fiducials 2502 and 2504, reference sensors 250 and/or biosensors 202 and the wavelength reflected by the biosensors 202 without requiring any scanned motion (note 1: only biosensors 202 are shown in the microplate 206) (note 2: the vision system 2900 can illuminate all or a certain number of the biosensors 202 in the microplate 206). In fact, the computer 2916 can process the recorded data to locate the edges of the fiducials 2502 and 2504, reference sensors 250 and/or biosensors 206 in the same manner as with the aforementioned scanned methods 100 and 1800. When a microplate 206 is removed from the holder 208 and then reinserted, a second set of position measurements can be made and subsequently the same plate position information ($\Delta x$, $\Delta y$, $\Delta \theta$, delay$_t$, and $\Delta \phi$) as was used with the aforementioned scanned methods 100 and 1800 can be calculated. The plate position information can then be used to adjust the position of the microplate 206 or the camera 2902 to minimize/correct the position deviation of the biosensors 202, and then the vision system 2900 can be used to record a second wavelength measurement. For a more detailed discussion about the basic configuration and some additional components associated with this exemplary vision system 2900 reference is made to U.S. patent application Ser. No. 11/711,207 entitled "Swept Wavelength Imaging Optical Interrogation System and Method for Using Same" (the contents of which are hereby incorporated by reference herein).

From the foregoing it should be appreciated that the optical interrogation system 200 (or other optical interrogation systems which can also implement methods 100 and 2800) typically use a small diameter optical beam (e.g., 0.1 mm) to spatially scan the biosensors 202 (and the reference sensors 250 if used). Such an optical beam 224 traverses all the biosensors 202 in a row of a microplate 206, i.e. 24 sensor elements for a 384 well format microplate 206. So, when scanning an entire microplate 206, the optical interrogation system 200 receives reflected power as a function of scan position that is close to zero when the optical beam 224 is off a biosensor 202, and close to a maximum governed by the reflectivity of the biosensor 202 when the optical beam 224 is on a biosensor 202 (see FIG. 5). Then, by detecting these zero to maximum reflected power transitions while scanning, it is possible to deduce the positions of the biosensors 202. As is described in U.S. patent application Ser. No. 11/210,920, to obtain 2-dimensional information on sensor positions, one can use a one-dimensional scan combined with some fiducial features/edges at an angle with respect to the scanning direction such as triangular or trapezoidal biosensors 202. Once, the microplate 206 is scanned, then the location of the biosensors 202 may be recorded. Upon subsequent reads or reinsertions of the microplate 206, the process is repeated, and the new locations of the biosensors 202 are compared to the old locations. All of the biosensors 202 on a microplate 206 may be scanned by using multiple optical beams 224, for example 16 optical beams 224 can be used to interrogate the 16 rows of a 384 well microplate 206.

In this invention, it was detailed how to process this position information, and specifically the position change data, so that a correction may be applied to either the position of the optical beam 224 or to the position of the microplate 206. In particular, the position information that was calculated included global displacement in x, a global displacement in y, and plate rotation. Also, depending on the hardware design of the optical interrogation system 200, phase delays for the optical beams 224 which scan the different rows of the microplate 206 could be calculated, and possibly even biosensor 202 to biosensor 202 pitch may be calculated to accommodate thermal dilations. Additionally, there was a description provided herein as to how it may be important to use a sufficiently small spatial sampling of the reflected power such that pixelation related non-linearities in the determination of the positions of the biosensors 202 can be kept sufficiently small.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. A method for interrogating biosensors located within wells of a microplate, said method comprising the steps of:
   placing said microplate onto a holder;
   scanning multiple optical beams across multiple rows of the biosensors within said microplate to determine a first position of said microplate and to obtain a first set of interrogation measurements;
   removing said microplate from said holder;
   re-inserting said microplate back onto said holder;
   re-scanning the multiple optical beams across the multiple rows of the biosensors within said microplate to determine a second position of said microplate;
   determining a position deviation of the microplate by comparing the first position and the second position of said microplate, wherein the position deviation of the microplate is determined by using biosensor displacements $(\Delta x_{ij}, \Delta y_{ij})$ which are determined from absolute biosensor positions $(x_{ij}, y_{ij})$ relative to a single biosensor A1 measured during the scanning step and the re-scanning step where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:
      a global x-displacement $(\Delta x)$ value of said microplate;
      a global y-displacement $(\Delta y)$ value of said microplate; and
      a microplate rotation $(\Delta\theta)$ value;
   calculating a scan trajectory to take into account the position deviation of the microplate;
   re-scanning the multiple optical beams using the calculated scan trajectory over the multiple rows of the biosensors within said microplate to obtain a second set of interrogation measurements; and
   comparing the first set of interrogation measurements and the second set of interrogation measurements to determine whether or not a biological substance is present or a biomolecular event occurred on one or more of the biosensors within said microplate.

2. The method of claim 1, wherein said scanning step is performed in two separate scanning steps where one scanning step is performed to determine the first position of said microplate and the other scanning step is performed to obtain the first set of interrogation measurements.

3. The method of claim 1, wherein said scanning step, said re-scanning steps and said comparing step are performed for each row of the biosensor(s) within said microplate.

4. The method of claim 1, wherein said step of determining the position deviation of the microplate further includes calculating a thermally induced dimensional change $(\Delta\phi)$ value or other dimensional expansion or contraction value of either the microplate or a position encoder that is associated with a motion stage.

5. The method of claim 1, wherein if there is a microplate rotation $(\Delta\theta)$ value then perform the step of adjusting a position of the microplate to take into account the rotational deviation of the microplate.

6. The method of claim 1, wherein if there is a microplate rotation $(\Delta\theta)$ value then perform a step of introducing a per optical channel position/time delay before initiating the second re-scanning step to acquire interrogating measurements for each row of the biosensors within the microplate to take into account the rotational deviation of the microplate.

7. The method of claim 1, wherein each biosensor has a diffraction grating with an angled edge or a non-responding angled line located thereon.

8. The method of claim 1, wherein during said scanning step and said re-scanning steps a predetermined pixel size in an imaging system is selected and used to help mitigate problematical pixelation induced non-linearities in the estimates of the biosensors or fiducial locations.

9. The method of claim 1, wherein said microplate is physically moved while multiple optical elements that emit the multiple optical beams remain in a stationary position during the performance of said scanning step and said re-scanning steps.

10. The method of claim 1, wherein said microplate remains in a stationary position while multiple optical elements that emit the multiple optical beams are physically moved during the performance of said scanning step and said re-scanning steps.

11. An optical interrogation system comprising:
   a holder for supporting a microplate;
   a light source for emitting multiple first optical beams which are scanned across multiple rows of biosensors within wells of said microplate;
   an optical detection system for collecting the scanned first optical beams which are reflected from the multiple rows of the biosensors within said microplate;
   a processor for analyzing the collected first optical beams and determining a first position of said microplate;
   said light source for emitting multiple second optical beams which are scanned across the multiple rows of the biosensors within said microplate;
   said optical detection system for collecting the scanned second optical beams which are reflected from the multiple rows of the biosensors sensors within said microplate;
   said light source for emitting multiple third optical beams which are scanned across the multiple rows of the biosensors within said microplate;
   said optical detection system for collecting the scanned third optical beams which are reflected from the multiple rows of the biosensors within said microplate;
   said processor for analyzing the collected third optical beams and determining a second position of said microplate;
   said processor for determining a position deviation of the microplate by comparing the first position and the second position of said microplate, wherein the position deviation of the microplate is determined by using biosensor displacements $(\Delta x_{ij}, \Delta y_{ij})$ which are determined from absolute biosensor positions $(x_{ij}, y_{ij})$ relative to a single biosensor A1 measured during the scanning steps where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:

a global x-displacement (Δx) value of said microplate;
a global y-displacement (Δy) value of said microplate; and
a microplate rotation (Δθ) value;
said processor for calculating a scan trajectory to take into account a position deviation of the microplate;
said light source for creating multiple fourth optical beams which are scanned according to the calculated scan trajectory across the multiple rows of the biosensors within said microplate;
said optical detection system for collecting the scanned fourth optical beams which are reflected from the multiple rows of the biosensors within said microplate; and
said processor for comparing the results of the second scanning of the multiple rows of the biosensors to the results of the fourth scanning of the multiple rows of the biosensors to determine whether or not a biological substance is present or a biomolecular event occurred on the multiple rows of the one or more biosensors within said microplate.

12. The optical interrogation system of claim 11, wherein said processor further determines the thermally induced dimensional change (Δφ) value or other dimensional expansion or contraction value of either the microplate or a position encoder that is associated with a motion stage.

13. The optical interrogation system of claim 11, wherein said processor controls an adjustment of the holder when there is a microplate rotation (Δθ) value to take into account the rotational deviation of the microplate.

14. The optical interrogation system of claim 11, wherein said processor introduces a per optical channel position/time delay before initiating the second re-scanning step to acquire interrogating measurements for each row of the biosensors within the microplate when there is a microplate rotation (Δθ) value to take into account the rotational deviation of the microplate.

15. A method for interrogating biosensors located within wells of a microplate, said method comprising the steps of:
placing said microplate onto a holder;
scanning multiple optical beams across multiple rows of fiducial markings/reference sensors within said microplate to determine a first position of said microplate;
scanning the multiple optical beams across multiple rows of the biosensors within said microplate to obtain a first set of interrogation measurements;
removing said microplate from said holder;
re-inserting said microplate back onto said holder;
re-scanning the multiple optical beams across the multiple rows of the fiducial markings/reference sensors within said microplate to determine a second position of said microplate;
determining a position deviation of the microplate by comparing the first position and the second position of said microplate, wherein the position deviation of the microplate is determined by using fiducial markings/reference sensors displacements $(\Delta x_{ij}, \Delta y_{ij})$ which are determined from absolute fiducial markings/reference sensors positions $(x_{ij}, y_{ij})$ relative to a single fiducial markings/reference sensors A1 measured during the scanning step and the re-scanning step where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:

a global x-displacement (Δx) value of said microplate;
a global y-displacement (Δy) value of said microplate; and
a microplate rotation (Δθ) value;
calculating a scan trajectory to take into account the position deviation of the microplate;
re-scanning the multiple optical beams using the calculated scan trajectory over the multiple rows of biosensors within said microplate to obtain a second set of interrogation measurements; and
comparing the first set of interrogation measurements and the second set of interrogation measurements to determine whether or not a biological substance is present or a biomolecular event occurred on one or more of the biosensors within said microplate.

16. The method of claim 15, wherein said scanning steps, said re-scanning steps and said comparing step are performed for each row of the fiducial marking(s)/reference sensor(s) and/or the biosensor(s) within said microplate.

17. The method of claim 15, wherein said step of determining the position deviation of the microplate further includes calculating the thermally induced dimensional change (Δφ) value or other dimensional expansion or contraction value of either the microplate or a position encoder that is associated with a motion stage.

18. The method of claim 15, wherein if there is a microplate rotation (Δθ) value then perform the step of adjusting a position of the microplate to take into account the rotational deviation of the microplate.

19. The method of claim 15, wherein if there is a microplate rotation (Δθ) value then perform a per optical channel position/time delay before initiating the second re-scanning step to acquire interrogating measurements for each row of the biosensors within the microplate to take into account the rotational deviation of the microplate.

20. The method of claim 15, wherein each fiducial marking/reference sensor has a diffraction grating with an angled edge or a non-responding angled line located thereon.

21. The method of claim 15, wherein each fiducial marking/reference sensor has a reflectivity and wavelength that is similar to the reflectivity and wavelength of the biosensor(s).

22. The method of claim 15, wherein each fiducial marking/reference sensor is located outside of a well in the microplate.

23. The method of claim 15, wherein during said scanning steps and said re-scanning steps a predetermined pixel size in an imaging system is selected and used to help mitigate problematical pixelation induced non-linearities.

24. An optical interrogation system comprising:
a holder for supporting a microplate;
a light source for multiple first optical beams which are scanned across multiple rows of one or more fiducial markings/reference sensors within said microplate;
an optical detection system for collecting the scanned first optical beams which are reflected from the multiple rows of the one or more fiducial markings/reference sensors within said microplate;
a processor for analyzing the collected first optical beams and determining a first position of said microplate;
said light source for emitting multiple second optical beams which are scanned across the multiple rows of one or more biosensors within wells of said microplate;
said optical detection system for collecting the scanned second optical beams which are reflected from the multiple rows of the one or more biosensors within said microplate;

said light source for emitting multiple third optical beams which are scanned across the multiple rows of the one or more fiducial markings/reference sensors within said microplate;

said optical detection system for collecting the scanned third optical beams which are reflected from the multiple rows of the one or more fiducial markings/reference sensors within said microplate;

said processor for analyzing the collected third optical beams and determining a second position of said microplate;

said processor for determining a position deviation of the microplate by comparing the first position and the second position of said microplate, wherein the position deviation of the microplate is determined b usin fiducial markings/reference sensors displacements ($\Delta x_{ij}$, $\Delta y_{ij}$) which are determined from absolute fiducial markings/reference sensors positions ($x_{ij}$, $y_{ij}$) relative to a single fiducial markings/reference sensors A1 measured during the scanning steps where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:
a global x-displacement ($\Delta x$) value of said microplate;
a global y-displacement ($\Delta y$) value of said microplate; and
a microplate rotation ($\Delta\theta$) value;

said processor for calculating a scan trajectory to take into account a position deviation of the microplate;

said light source for creating multiple fourth optical beams which are scanned according to the calculated scan trajectory across the multiple rows of the one or more biosensors within said microplate;

said optical detection system for collecting the scanned fourth optical beams which are reflected from the multiple rows of the one or more biosensors within said microplate; and said processor for comparing the results of the first scanning of the multiple rows of the one or more biosensors to the results of the second scanning of the multiple rows of the one or more biosensors to determine whether or not a biological substance is present or a biomolecular event occurred on the multiple rows of the one or more biosensors within said microplate.

25. The optical interrogation system of claim 24, wherein said processor further determines the position deviation of the microplate by calculating the thermally induced dimensional change ($\Delta\phi$) value or other dimensional expansion or contraction value of either the microplate or a position encoder that is associated with a motion stage.

26. The optical interrogation system of claim 24, wherein said processor controls an adjustment of the holder when there is a microplate rotation ($\Delta\theta$) value to take into account the rotational deviation of the microplate.

27. The optical interrogation system of claim 24, wherein said processor introduces a per optical channel position/time delay before initiating the second re-scanning step to acquire interrogating measurements for each row of the one or more biosensors within the microplate when there is a microplate rotation ($\Delta\theta$) value to take into account the rotational deviation of the microplate.

28. A method for interrogating biosensors located within wells of a microplate, said method comprising the steps of:
placing said microplate onto a holder;
illuminating one or more of the biosensors within said microplate to determine a first position of said microplate and to obtain a first set of interrogation measurements;
removing said microplate from said holder;
re-inserting said microplate back onto said holder;
re-illuminating the one or more biosensors within said microplate to determine a second position of said microplate;
determining a position deviation of the microplate by comparing the first position and the second position of said microplate, wherein the position deviation of the microplate is determined by using biosensor displacements ($\Delta x_{ij}$, $\Delta y_{ij}$) which are determined from absolute biosensor positions ($x_{ij}$, $y_{ij}$) relative to a single biosensor A1 measured during the illuminating step and the re-illuminating step where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:
a global x-displacement ($\Delta x$) value of said microplate;
a global v-displacement ($\Delta y$) value of said microplate; and
a microplate rotation ($\Delta\theta$) value;
taking into account the position deviation of the microplate;
re-illuminating the one or more biosensors within said microplate to obtain a second set of interrogation measurements; and
comparing the first set of interrogation measurements and the second set of interrogation measurements to determine whether or not a biological substance is present or a biomolecular event occurred on one or more of the biosensors within said microplate.

29. The method of claim 28, wherein said microplate further includes fiducial markings/reference sensors which are used to determine the first position and the second position of the microplate.

30. The method of claim 28, wherein said step of determining the position deviation of the microplate further includes calculating a thermally induced dimensional change ($\Delta\phi$) value or other dimensional expansion or contraction value of either the microplate or a position encoder that is associated with a motion stage.

31. An optical interrogation system comprising:
a holder for supporting a microplate;
an optical system that illuminates one or more biosensors within wells of said microplate;
an imaging detection system that collects reflected light from the one or more of the biosensors within said microplate;
a processor that analyzes the collected reflected light and determines a first position of said microplate and obtains a first set of interrogation measurements;
said optical system re-illuminates the one or more of the biosensors within said microplate after the microplate has been removed from said holder and re-inserted back in said holder;
said imaging detection system collects the second reflected light from the one or more of the biosensors within said microplate;
said processor analyzes the collected second reflected light and determines a second position of said microplate;
said processor determines a position deviation of the microplate by comparing the first position and the second position of said microplate, wherein the position deviation of the microplate is determined by using biosensor displacements ($\Delta x_{ij}$, $\Delta y_{ij}$) which are determined from absolute biosensor positions ($x_{ij}$, $y_{ij}$) relative to a single biosensor A1 measured during the illuminating step and the re-illuminating step where (i, j) denote (row, column) indices of the wells and by using two equations $\Delta x_{ij} \approx \Delta\theta \cdot (y_{ij}) + \langle \Delta x \rangle$ and $\Delta y_{ij} \approx \Delta\theta \cdot (x_{ij}) + \langle \Delta y \rangle$ to obtain:
a global x-displacement ($\Delta x$) value of said microplate;
a global y-displacement ($\Delta y$) value of said microplate; and
a microplate rotation ($\Delta\theta$) value;
said processor re-positions the microplate or the optical detection system to take into account a position deviation of the microplate;
said optical system re-illuminates the one or more of the biosensors within said microplate;
said imaging detection system collects the third reflected light from the one or more of the biosensors within said microplate;
said processor analyzes the collected third reflected light and obtains a second set of interrogation measurements; and said processor compares the first set of interrogation measurements and the second set of interrogation measurements to determine whether or not a biological substance is present or a biomolecular event occurred on one or more of the biosensors within said microplate.

32. The optical interrogation system of claim 31, wherein said microplate further includes fiducial markings/reference sensors which are used to determine the first position and the second position of the microplate.

33. The optical interrogation system of claim 31, wherein said processor further determines the thermally induced dimensional change ($\Delta\phi$) value or other dimensional expansion or contraction value of either the microplate or a position encoder that is associated with a motion stage.

* * * * *

UNITED STATES PATENT AND TRADEMARK OFFICE
CERTIFICATE OF CORRECTION

| | |
|---|---|
| PATENT NO. | : 7,830,513 B2 |
| APPLICATION NO. | : 11/900315 |
| DATED | : November 9, 2010 |
| INVENTOR(S) | : Michael Joseph Dailey, Jr. et al. |

Page 1 of 1

It is certified that error appears in the above-identified patent and that said Letters Patent is hereby corrected as shown below:

On the Title page:

| Col. | Line | |
|---|---|---|
| 2 | | item (74) Attorney, Agent, or Firm – Gregory B. Butler, Thomad R. Beall; Should say (74) Attorney, Agent, or Firm – Gregory B. Butler, Thomas R. Beall. |
| 19 | 15 | Reads: "deviation of the microplate is determined b usin fiducial" Should read: "deviation of the microplate is determined by using fiducial" |

Signed and Sealed this
First Day of February, 2011

David J. Kappos
*Director of the United States Patent and Trademark Office*